United States Patent
Sahin et al.

(10) Patent No.: US 10,858,415 B2
(45) Date of Patent: Dec. 8, 2020

(54) PEPTIDE MIMOTOPES OF CLAUDIN 18.2 AND USES THEREOF

(71) Applicants: BioNTech AG, Mainz (DE); TRON—Translationale Onkologie an der Universitatsmedizin der Johannes Gutenberg—Universitat Mainz gemeinnutzige GmbH, Mainz (DE); Universitatsmedizin der Johannes Gutenberg—Universitat Mainz, Mainz (DE); JPT Peptide Technologies GmbH, Berlin (DE)

(72) Inventors: Ugur Sahin, Mainz (DE); Matin Daneschdar, Budenheim (DE); Hans-Ulrich Schmoldt, Klein-Winternheim (DE); Laura-Marie Kring (née Plum), Mainz (DE); Markus Fiedler, Halle an der Saale (DE); Ulf Reimer, Berlin (DE); Karsten Schnatbaum, Berlin (DE)

(73) Assignees: TRON—TRANSLATIONALE ONKOLOGIE AN DER UNIVERSITATSMEDIZIN DER JOHANNES GUTTENBERG-UNIVERSITAT MAINZ GEMEINNUIZIGE GMBH, Mainz (DE); JPT PEPTIDE TECHNOLOGIES GMBH, Berlin (DE); BIONTECH SE, Mainz (DE)

( * ) Notice: Subject to any disclaimer, the term of this patent is extended or adjusted under 35 U.S.C. 154(b) by 1167 days.

(21) Appl. No.: 15/113,981

(22) PCT Filed: Jan. 29, 2014

(86) PCT No.: PCT/EP2014/000244
§ 371 (c)(1),
(2) Date: Jul. 25, 2016

(87) PCT Pub. No.: WO2015/113576
PCT Pub. Date: Aug. 6, 2015

(65) Prior Publication Data
US 2016/0347815 A1 Dec. 1, 2016

(51) Int. Cl.
| | | |
|---|---|---|
| *A61K 38/08* | (2019.01) | |
| *A61K 38/12* | (2006.01) | |
| *C07K 5/00* | (2006.01) | |
| *A61K 38/04* | (2006.01) | |
| *C07K 7/00* | (2006.01) | |
| *C07K 16/00* | (2006.01) | |
| *C07K 17/00* | (2006.01) | |
| *C07K 14/705* | (2006.01) | |
| *C07K 7/64* | (2006.01) | |
| *A61K 39/00* | (2006.01) | |
| *G01N 33/53* | (2006.01) | |
| *G01N 33/574* | (2006.01) | |

(52) U.S. Cl.
CPC ............ *C07K 14/705* (2013.01); *A61K 38/08* (2013.01); *A61K 38/12* (2013.01); *A61K 39/0005* (2013.01); *C07K 7/64* (2013.01); *G01N 33/5308* (2013.01); *G01N 33/57492* (2013.01); *G01N 2333/705* (2013.01); *G01N 2500/02* (2013.01); *G01N 2500/04* (2013.01)

(58) Field of Classification Search
None
See application file for complete search history.

(56) References Cited

U.S. PATENT DOCUMENTS

2005/0214852 A1    9/2005  Gaynor et al.

FOREIGN PATENT DOCUMENTS

| WO | WO1998016549 A1 | 4/1998 |
| WO | WO2007007116 | 1/2007 |
| WO | WO2012068236 | 5/2012 |
| WO | WO 2015/113576 A1 | 8/2015 |

OTHER PUBLICATIONS

Joseph-Horne et al., FEBS Lett. 481:141-146 (2000) (Year: 2000).*
Adessi et al., Curr. Med. Chem. 9:963-978 (2002) (Year: 2002).*
Sato et al., FEBS J. 279:2262-2271 (2012) (Year: 2012).*
Terpe, K., Appl. Microbiol. Biotechnol. 60:523-533 (2003) (Year: 2003).*
Leroch et al., Appl. Environ. Microbiol. 77:2887-2897 (2011) (Year: 2011).*
EMBL Database, Accession No. EBN30347, 2 pages (2007) (Year: 2007).*

(Continued)

*Primary Examiner* — Thea D' Ambrosio
(74) *Attorney, Agent, or Firm* — Neal, Gerber & Eisenberg LLP; Kevin A. O'Connor

(57) ABSTRACT

The present invention provides molecules that mimic antigenic determinants of the integral transmembrane protein claudin 18.2 (CLDN18.2). These molecules compete with CLDN18.2 for binding to a CLDN18.2 binding domain, e.g. a CLDN18.2 binding domain of an antibody, and are capable of detecting antibodies against CLDN18.2. The mimotopes of the invention may be used to generate or inhibit immune responses in animals and preferably humans. Furthermore, they can be used for purposes of detecting agents comprising a CLDN18.2 binding domain in biological samples as well as for purifying agents comprising a CLDN18.2 binding domain.

15 Claims, 7 Drawing Sheets
Specification includes a Sequence Listing.

(56) References Cited

OTHER PUBLICATIONS

EMBL Database, Accession No. GBN50079, 2 pages (2019) (Year: 2019).*

Schnatbaum et al., Biotechnol. J. 9:545-554 (2014) (Year: 2014).*

Masood Jelokhani-Niaraki et al., "Diastereoisomeric analogues of gramicidin S: structure. biological activity and interaction with lipid bilayers", Biochem. J., Jan. 1, 2000. pp. 747-755.

Alan C. Gibbs et al: "Unusual [beta]-sheet periodicity in small cyclic peptides". Nature Structural Biology. vol. 5. No. 4. Apr. 1, 1998. pp. 284-288.

Frecer et al: "QSAR analysis of antimicrobial and haemolytic effects of cyclic cationic antimicrobial peptides derived from protegrin-I". Bioorganic & Medicinal Chemistry. vol. 14. No. 17. Sep. 1, 2006. pp. 6065-6074.

Database UniProt [Online], Jul. 19, 2005. "SubName: Full= Uncharacterized protein;". XP002721329.accession No. UniProt:Q4QAP3 Database accession No. Q4QAP3 sequence.

Database UniProt [Online], Jul. 19, 2005. "SubName: Full= Uncharacterized protein;".XP002721330.accession No. UniProt:Q4QIG7 Database accession No. Q4QIG7 sequence.

Database UniProt [Online], Oct. 1, 2003. "SubName: Full=Metallo-beta-lactamase superfamily:Flavin reductase-like domain;"XP002721331. accession No. UniProt:Q7TUJ5, Database accession No. Q7TUJ5 sequence.

Database UniProt [Online], Mar. 1, 2003. "SubName: Full=Putative uncharacterized protein PF14 0731;". XP002721332.accession No. UniProt:Q8IK76 Database accession No. Q8IK76 sequence.

Database UniParc [Online], Oct. 24, 2013. "Poribacteria bacterium WGA-3G". XP002721333. retrieved from Uniprot Database accession No. UPI0003B732CO sequence.

Database UniParc [Online], Apr. 11, 2007. "Marine metagenome". XP002721334.retrieved from Uniprot Database accession No. UPI00011491B9 sequence.

Database UniParc [Online], Mar. 18, 2013. "Tepidanaerobacter acetatoxydans (strain DSM 21804 /JCM 16047 /Refl)". XP002721335. retrieved from Uniprot Database accession No. UPI0003019FOD sequence.

Database UniParc [Online], Oct. 27, 2011, "Cricetulus griseus (Chinese hamster) (Cricetulus barabensis griseus)", XP002721336, retrieved from Uniprot Database accession No. UPI00022F4FBB sequence.

Database UniProt [Online], Jul. 24, 2013, "SubName: Full= Uncharacterized protein;", XP002721337,accession No. UniProt:R9K409, Database accession No. R9K409 sequence.

Database UniProt [Online], Jun. 13, 2012, "SubName: Full= Uncharacterized protein;", XP002721338,accession No. UniProt:IOXL36, Database accession No. IOXL36 sequence.

Database UniProt [Online], Oct. 19, 2011, "SubName: Full= Putative uncharacterized protein;", XP002721339, accession No. UniProt:GOPHMI, Database accession No. GOPHMI sequence.

Casey Joanne L et al: "Phage display of peptides in ligand selection for use in affinity chromatography", Methods in Molecular Biology, vol. 421, Jan. 1, 2008, pp. 111-124.

Damen Carola W N et al: "Bioanalytical methods for the quantification of therapeutic monoclonal antibodies and their application in clinical pharmacokinetic studies". Human Antibodies. vol. 18. No. 3. Jan. 1, 2009. pp. 47-73.

Stefan Woll et al: "Claudin 18.2 is a target for IMAB362 antibody in pancreatic neoplasms". International Journal of Cancer. Sep. 16, 2013. pp. 1-9.

Sahin Ugur et al: "Claudin-18 splice variant 2 is a pan-cancer target suitable for therapeutic antibody development". Clinical Cancer Research. vol. 14. No. 23. Dec. 1, 2008. pp. 7624-7634.

Karsten Schnatbaum et al: "Peptide microarrays enable rapid mimotope optimization for pharmacokinetic analysis of the novel therapeutic antibody IMAB362", Biotechnology Journal. Feb. 4, 2014. pp. 1-19.

European Patent Office, International Search Report for International Application No. PCT/EP2014/000244 (dated May 12, 2014).

European Patent Office, Written Opinion for International Application No. PCT/EP2014/000244 (dated May 12, 2014).

* cited by examiner

C7C-8  ACHLGYPGRCGGGS (SEQ ID NO:76)
C7C-11 ACHYSYPGVCGGGS (SEQ ID NO:77)
C7C-13 ACHLNYPGYCGGGS (SEQ ID NO:78)
C7C-15 ACHLRYPGECGGGS (SEQ ID NO:79)
C7C-18 ACYKGYPGYCGGGS (SEQ ID NO:80)

SEQUENCE LISTING

<160> NUMBER OF SEQ ID NOS: 80

<210> SEQ ID NO 1

```
<211> LENGTH: 261
<212> TYPE: PRT
<213> ORGANISM: Homo sapiens

<400> SEQUENCE: 1

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 2
<211> LENGTH: 118
<212> TYPE: PRT
<213> ORGANISM: Artificial Sequence
<220> FEATURE:
<223> OTHER INFORMATION: Antibody fragment

<400> SEQUENCE: 2

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
50                  55                  60
```

```
Lys Asp Lys Ala Thr Leu Thr Val Asp Lys Ser Ser Thr Ala Tyr
 65                  70                  75                  80

Met Gln Leu Ser Ser Pro Thr Ser Glu Asp Ser Ala Val Tyr Tyr Cys
                 85                  90                  95

Thr Arg Ser Trp Arg Gly Asn Ser Phe Asp Tyr Trp Gly Gln Gly Thr
            100                 105                 110

Thr Leu Thr Val Ser Ser
        115
```

<210> SEQ ID NO 3
<211> LENGTH: 113
<212> TYPE: PRT
<213> ORGANISM: Artificial Sequence
<220> FEATURE:
<223> OTHER INFORMATION: Antibody fragment

<400> SEQUENCE: 3

```
Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Phe Thr Phe Gly Ser Gly Thr Lys Leu Glu Ile
            100                 105                 110

Lys
```

<210> SEQ ID NO 4
<211> LENGTH: 15
<212> TYPE: PRT
<213> ORGANISM: Artificial Sequence
<220> FEATURE:
<223> OTHER INFORMATION: Linker

<400> SEQUENCE: 4

```
Gly Gly Gly Gly Ser Gly Gly Gly Gly Ser Gly Gly Gly Gly Ser
 1               5                  10                  15
```

<210> SEQ ID NO 5
<211> LENGTH: 16
<212> TYPE: PRT
<213> ORGANISM: Artificial Sequence
<220> FEATURE:
<223> OTHER INFORMATION: Linker

<400> SEQUENCE: 5

```
Val Glu Gly Gly Gly Gly Ser Gly Gly Gly Gly Ser Gly Gly Val Asp
 1               5                  10                  15
```

<210> SEQ ID NO 6
<211> LENGTH: 6
<212> TYPE: PRT
<213> ORGANISM: Artificial Sequence
<220> FEATURE:
<223> OTHER INFORMATION: Linker

```
<400> SEQUENCE: 6

Ser Gly Gly Gly Gly Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Linker

<400> SEQUENCE: 7

Gly Gly Gly Gly Ser
1               5

<210> SEQ ID NO 8
<211> LENGTH: 18
<212> TYPE: PRT
<213> ORGANISM: Artificial Sequence
<220> FEATURE:
<223> OTHER INFORMATION: Linker

<400> SEQUENCE: 8

Val Glu Gly Gly Ser Gly Gly Ser Gly Gly Ser Gly Gly Ser Gly Gly
1               5                   10                  15

Val Asp

<210> SEQ ID NO 9
<211> LENGTH: 20
<212> TYPE: PRT
<213> ORGANISM: Artificial Sequence
<220> FEATURE:
<223> OTHER INFORMATION: Linker

<400> SEQUENCE: 9

Gly Gly Gly Gly Ser Gly Gly Gly Ser Gly Gly Gly Gly Ser Gly
1               5                   10                  15

Gly Gly Gly Ser
            20

<210> SEQ ID NO 10
<211> LENGTH: 25
<212> TYPE: PRT
<213> ORGANISM: Artificial Sequence
<220> FEATURE:
<223> OTHER INFORMATION: Linker

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 11
<211> LENGTH: 18
<212> TYPE: PRT
<213> ORGANISM: Artificial Sequence
<220> FEATURE:
<223> OTHER INFORMATION: Linker

<400> SEQUENCE: 11

Gly Gly Gly Gly Ser Gly Gly Ser Gly Gly Ser Gly Gly Ser Gly Gly
1               5                   10                  15

Gly Ser
```

<210> SEQ ID NO 12
<211> LENGTH: 467
<212> TYPE: PRT
<213> ORGANISM: Artificial Sequence
<220> FEATURE:
<223> OTHER INFORMATION: Description of artificial sequence: chimeric monoclonal antibody

<400> SEQUENCE: 12

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val

```
                355                 360                 365
Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 13
<211> LENGTH: 240
<212> TYPE: PRT
<213> ORGANISM: Artificial Sequence
<220> FEATURE:
<223> OTHER INFORMATION: Description of artificial sequence: chimeric
      monoclonal antibody

<400> SEQUENCE: 13

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
                20                  25                  30

Val Thr Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
                100                 105                 110

Tyr Cys Gln Asn Asp Tyr Ser Tyr Pro Phe Thr Phe Gly Ser Gly Thr
            115                 120                 125

Lys Leu Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

-continued

```
<210> SEQ ID NO 14
<211> LENGTH: 7
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Any amino acid, preferably an amino acid
      selected from the group consisting of Gln, His, Tyr, Lys and Met,
      more preferably an amino acid selected from the group consisting
      of Gln, His and Tyr
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Pro, Leu, Lys, Tyr, Phe and
      Arg, more preferably an amino acid selected from the group
      consisting of Pro, Leu, Lys and Tyr
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Ala, Gly, Asn, Arg, Ser,
      Lys, Trp, Phe and Tyr, more preferably an amino acid selected from
      the group consisting of Ala, Gly, Asn, Arg and Ser
<220> FEATURE:
<221> NAME/KEY: MISC_FEATURE
<222> LOCATION: (5)..(5)
<223> OTHER INFORMATION: Any amino acid, preferably an amino acid
      selected from the group consisting of Tyr, Pro and Arg, more
      preferably an amino acid selected from the group consisting of Tyr
      and Pro
<220> FEATURE:
<221> NAME/KEY: MISC_FEATURE
<222> LOCATION: (6)..(6)
<223> OTHER INFORMATION: Any amino acid, preferably an amino acid
      selected from the group consisting of His, Gly, Lys and Arg, more
      preferably an amino acid selected from the group consisting of His
      and Gly
<220> FEATURE:
<221> NAME/KEY: MISC_FEATURE
<222> LOCATION: (7)..(7)
<223> OTHER INFORMATION: Any amino acid, preferably an amino acid
      selected from the group consisting of Thr, Trp, Tyr, Glu, Arg,
      Val, Ile, Leu, Met, Ala, Phe and Lys, more preferably an amino
      acid selected from the group consisting of Thr, Trp, Tyr, Glu, Arg
      and Val

<400> SEQUENCE: 14

Xaa Xaa Xaa Tyr Xaa Xaa Xaa
1               5

<210> SEQ ID NO 15
<211> LENGTH: 9
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Gln, His, Tyr, Lys and Met,
      more preferably an amino acid selected from the group consisting
      of Gln, His and Tyr
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Pro, Leu, Lys, Tyr, Phe and
      Arg, more preferably an amino acid selected from the group
      consisting of Pro, Leu, Lys and Tyr
<220> FEATURE:
<221> NAME/KEY: MISC_FEATURE
```

```
<222> LOCATION: (4)..(4)
<223> OTHER INFORMATION: Any amino acid, preferably an amino acid
      selected from the group consisting of Ala, Gly, Asn, Arg, Ser,
      Lys, Trp, Phe and Tyr, more preferably an amino acid selected from
      the group consisting of Ala, Gly, Asn, Arg and Ser
<220> FEATURE:
<221> NAME/KEY: MISC_FEATURE
<222> LOCATION: (6)..(6)
<223> OTHER INFORMATION: Any amino acid, preferably an amino acid
      selected from the group consisting of Tyr, Pro and Arg, more
      preferably an amino acid selected from the group consisting of Tyr
      and Pro
<220> FEATURE:
<221> NAME/KEY: MISC_FEATURE
<222> LOCATION: (7)..(7)
<223> OTHER INFORMATION: Any amino acid, preferably an amino acid
      selected from the group consisting of His, Gly, Lys and Arg, more
      preferably an amino acid selected from the group consisting of His
      and Gly
<220> FEATURE:
<221> NAME/KEY: MISC_FEATURE
<222> LOCATION: (8)..(8)
<223> OTHER INFORMATION: Any amino acid, preferably an amino acid
      selected from the group consisting of Thr, Trp, Tyr, Glu, Arg,
      Val, Ile, Leu, Met, Ala, Phe and Lys, more preferably an amino
      acid selected from the group consisting of Thr, Trp, Tyr, Glu, Arg
      and Val

<400> SEQUENCE: 15

Cys Xaa Xaa Xaa Tyr Xaa Xaa Xaa Cys
1               5

<210> SEQ ID NO 16
<211> LENGTH: 10
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Gln, His, Tyr, Lys and Met,
      more preferably an amino acid selected from the group consisting
      of Gln, His and Tyr
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Pro, Leu, Lys, Tyr, Phe and
      Arg, more preferably an amino acid selected from the group
      consisting of Pro, Leu, Lys and Tyr
<220> FEATURE:
<221> NAME/KEY: MISC_FEATURE
<222> LOCATION: (5)..(5)
<223> OTHER INFORMATION: Any amino acid, preferably an amino acid
      selected from the group consisting of Ala, Gly, Asn, Arg, Ser,
      Lys, Trp, Phe and Tyr, more preferably an amino acid selected from
      the group consisting of Ala, Gly, Asn, Arg and Ser
<220> FEATURE:
<221> NAME/KEY: MISC_FEATURE
<222> LOCATION: (7)..(7)
<223> OTHER INFORMATION: Any amino acid, preferably an amino acid
      selected from the group consisting of Tyr, Pro and Arg, more
      preferably an amino acid selected from the group consisting of Tyr
      and Pro
<220> FEATURE:
<221> NAME/KEY: MISC_FEATURE
<222> LOCATION: (8)..(8)
<223> OTHER INFORMATION: Any amino acid, preferably an amino acid
      selected from the group consisting of His, Gly, Lys and Arg, more
      preferably an amino acid selected from the group consisting of His
      and Gly
<220> FEATURE:
<221> NAME/KEY: MISC_FEATURE
<222> LOCATION: (9)..(9)
<223> OTHER INFORMATION: Any amino acid, preferably an amino acid
```

```
         selected from the group consisting of Thr, Trp, Tyr, Glu, Arg,
         Val, Ile, Leu, Met, Ala, Phe and Lys, more preferably an amino
         acid selected from the group consisting of Thr, Trp, Tyr, Glu, Arg
         and Val

<400> SEQUENCE: 16

Ala Cys Xaa Xaa Xaa Tyr Xaa Xaa Xaa Cys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Any amino acid, preferably an amino acid
         selected from the group consisting of Gln, His, Tyr, Lys and Met,
         more preferably an amino acid selected from the group consisting
         of Gln, His and Tyr
<220> FEATURE:
<221> NAME/KEY: MISC_FEATURE
<222> LOCATION: (4)..(4)
<223> OTHER INFORMATION: Any amino acid, preferably an amino acid
         selected from the group consisting of Pro, Leu, Lys, Tyr, Phe and
         Arg, more preferably an amino acid selected from the group
         consisting of Pro, Leu, Lys and Tyr
<220> FEATURE:
<221> NAME/KEY: MISC_FEATURE
<222> LOCATION: (5)..(5)
<223> OTHER INFORMATION: Any amino acid, preferably an amino acid
         selected from the group consisting of Ala, Gly, Asn, Arg, Ser,
         Lys, Trp, Phe and Tyr, more preferably an amino acid selected from
         the group consisting of Ala, Gly, Asn, Arg and Ser
<220> FEATURE:
<221> NAME/KEY: MISC_FEATURE
<222> LOCATION: (7)..(7)
<223> OTHER INFORMATION: Any amino acid, preferably an amino acid
         selected from the group consisting of Tyr, Pro and Arg, more
         preferably an amino acid selected from the group consisting of Tyr
         and Pro
<220> FEATURE:
<221> NAME/KEY: MISC_FEATURE
<222> LOCATION: (8)..(8)
<223> OTHER INFORMATION: Any amino acid, preferably an amino acid
         selected from the group consisting of His, Gly, Lys and Arg, more
         preferably an amino acid selected from the group consisting of His
         and Gly
<220> FEATURE:
<221> NAME/KEY: MISC_FEATURE
<222> LOCATION: (9)..(9)
<223> OTHER INFORMATION: Any amino acid, preferably an amino acid
         selected from the group consisting of Thr, Trp, Tyr, Glu, Arg,
         Val, Ile, Leu, Met, Ala, Phe and Lys, more preferably an amino
         acid selected from the group consisting of Thr, Trp, Tyr, Glu, Arg
         and Val

<400> SEQUENCE: 17

Ala Cys Xaa Xaa Xaa Tyr Xaa Xaa Xaa Cys Gly
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Any amino acid, preferably an amino acid
         selected from the group consisting of Gln, His, Tyr, Lys and Met,
         more preferably an amino acid selected from the group consisting
```

```
            of His and Tyr
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Pro, Leu, Lys, Tyr, Phe and
      Arg, more preferably an amino acid selected from the group
      consisting of Leu, Lys, Tyr and Phe
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Ala, Gly, Asn, Arg, Ser,
      Lys, Trp, Phe and Tyr, more preferably an amino acid selected from
      the group consisting of Gly, Asn, Arg, Ser, Trp and Lys
<220> FEATURE:
<221> NAME/KEY: MISC_FEATURE
<222> LOCATION: (7)..(7)
<223> OTHER INFORMATION: Any amino acid, preferably an amino acid
      selected from the group consisting of Thr, Trp, Tyr, Glu, Arg,
      Val, Ile, Leu, Met, Ala, Phe and Lys

<400> SEQUENCE: 18

Xaa Xaa Xaa Tyr Pro Gly Xaa
1               5

<210> SEQ ID NO 19
<211> LENGTH: 9
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Any amino acid, preferably an amino acid
      selected from the group consisting of Gln, His, Tyr, Lys and Met,
      more preferably an amino acid selected from the group consisting
      of His and Tyr
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Pro, Leu, Lys, Tyr, Phe and
      Arg, more preferably an amino acid selected from the group
      consisting of Leu, Lys, Tyr and Phe
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Ala, Gly, Asn, Arg, Ser,
      Lys, Trp, Phe and Tyr, more preferably an amino acid selected from
      the group consisting of Gly, Asn, Arg, Ser, Trp and Lys
<220> FEATURE:
<221> NAME/KEY: MISC_FEATURE
<222> LOCATION: (8)..(8)
<223> OTHER INFORMATION: Any amino acid, preferably an amino acid
      selected from the group consisting of Thr, Trp, Tyr, Glu, Arg,
      Val, Ile, Leu, Met, Ala, Phe and Lys

<400> SEQUENCE: 19

Cys Xaa Xaa Xaa Tyr Pro Gly Xaa Cys
1               5

<210> SEQ ID NO 20
<211> LENGTH: 10
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Gln, His, Tyr, Lys and Met,
```

```
      more preferably an amino acid selected from the group consisting
      of His and Tyr
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Pro, Leu, Lys, Tyr, Phe and
      Arg, more preferably an amino acid selected from the group
      consisting of Leu, Lys, Tyr and Phe
<220> FEATURE:
<221> NAME/KEY: MISC_FEATURE
<222> LOCATION: (5)..(5)
<223> OTHER INFORMATION: Any amino acid, preferably an amino acid
      selected from the group consisting of Ala, Gly, Asn, Arg, Ser,
      Lys, Trp, Phe and Tyr, more preferably an amino acid selected from
      the group consisting of Gly, Asn, Arg, Ser, Trp and Lys
<220> FEATURE:
<221> NAME/KEY: MISC_FEATURE
<222> LOCATION: (9)..(9)
<223> OTHER INFORMATION: Any amino acid, preferably an amino acid
      selected from the group consisting of Thr, Trp, Tyr, Glu, Arg,
      Val, Ile, Leu, Met, Ala, Phe and Lys

<400> SEQUENCE: 20

Ala Cys Xaa Xaa Xaa Tyr Pro Gly Xaa Cys
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Any amino acid, preferably an amino acid
      selected from the group consisting of Gln, His, Tyr, Lys and Met,
      more preferably an amino acid selected from the group consisting
      of His and Tyr
<220> FEATURE:
<221> NAME/KEY: MISC_FEATURE
<222> LOCATION: (4)..(4)
<223> OTHER INFORMATION: Any amino acid, preferably an amino acid
      selected from the group consisting of Pro, Leu, Lys, Tyr, Phe and
      Arg, more preferably an amino acid selected from the group
      consisting of Leu, Lys, Tyr and Phe
<220> FEATURE:
<221> NAME/KEY: MISC_FEATURE
<222> LOCATION: (5)..(5)
<223> OTHER INFORMATION: Any amino acid, preferably an amino acid
      selected from the group consisting of Ala, Gly, Asn, Arg, Ser,
      Lys, Trp, Phe and Tyr, more preferably an amino acid selected from
      the group consisting of Gly, Asn, Arg, Ser, Trp and Lys
<220> FEATURE:
<221> NAME/KEY: MISC_FEATURE
<222> LOCATION: (9)..(9)
<223> OTHER INFORMATION: Any amino acid, preferably an amino acid
      selected from the group consisting of Thr, Trp, Tyr, Glu, Arg,
      Val, Ile, Leu, Met, Ala, Phe and Lys

<400> SEQUENCE: 21

Ala Cys Xaa Xaa Xaa Tyr Pro Gly Xaa Cys Gly
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Peptide mimotope

<400> SEQUENCE: 22

Gln Pro Ala Tyr Tyr His Thr
```

```
<210> SEQ ID NO 23
<211> LENGTH: 7
<212> TYPE: PRT
<213> ORGANISM: Artificial Sequence
<220> FEATURE:
<223> OTHER INFORMATION: Peptide mimotope

<400> SEQUENCE: 23

His Leu Gly Tyr Pro Gly Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Peptide mimotope

<400> SEQUENCE: 24

His Tyr Gly Tyr Pro Gly Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Peptide mimotope

<400> SEQUENCE: 25

His Leu Gly Tyr Pro Gly Trp
1               5

<210> SEQ ID NO 26
<211> LENGTH: 7
<212> TYPE: PRT
<213> ORGANISM: Artificial Sequence
<220> FEATURE:
<223> OTHER INFORMATION: Peptide mimotope

<400> SEQUENCE: 26

His Tyr Ser Tyr Pro Gly Val
1               5

<210> SEQ ID NO 27
<211> LENGTH: 7
<212> TYPE: PRT
<213> ORGANISM: Artificial Sequence
<220> FEATURE:
<223> OTHER INFORMATION: Peptide mimotope

<400> SEQUENCE: 27

His Tyr Gly Tyr Pro Gly Val
1               5

<210> SEQ ID NO 28
<211> LENGTH: 7
<212> TYPE: PRT
<213> ORGANISM: Artificial Sequence
<220> FEATURE:
<223> OTHER INFORMATION: Peptide mimotope

<400> SEQUENCE: 28

His Tyr Ser Tyr Pro Gly Trp
1               5
```

<210> SEQ ID NO 29
<211> LENGTH: 7
<212> TYPE: PRT
<213> ORGANISM: Artificial Sequence
<220> FEATURE:
<223> OTHER INFORMATION: Peptide mimotope

<400> SEQUENCE: 29

His Leu Arg Tyr Pro Gly Glu
1               5

<210> SEQ ID NO 30
<211> LENGTH: 7
<212> TYPE: PRT
<213> ORGANISM: Artificial Sequence
<220> FEATURE:
<223> OTHER INFORMATION: Peptide mimotope

<400> SEQUENCE: 30

His Tyr Arg Tyr Pro Gly Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Peptide mimotope

<400> SEQUENCE: 31

His Leu Asn Tyr Pro Gly Tyr
1               5

<210> SEQ ID NO 32
<211> LENGTH: 7
<212> TYPE: PRT
<213> ORGANISM: Artificial Sequence
<220> FEATURE:
<223> OTHER INFORMATION: Peptide mimotope

<400> SEQUENCE: 32

His Leu Gly Tyr Pro Gly Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: Peptide mimotope

<400> SEQUENCE: 33

His Leu Asn Tyr Pro Gly Trp
1               5

<210> SEQ ID NO 34
<211> LENGTH: 7
<212> TYPE: PRT
<213> ORGANISM: Artificial Sequence
<220> FEATURE:
<223> OTHER INFORMATION: Peptide mimotope

<400> SEQUENCE: 34

Tyr Lys Gly Tyr Pro Gly Tyr
1               5

```
<210> SEQ ID NO 35
<211> LENGTH: 7
<212> TYPE: PRT
<213> ORGANISM: Artificial Sequence
<220> FEATURE:
<223> OTHER INFORMATION: Peptide mimotope

<400> SEQUENCE: 35

His Tyr Gly Tyr Pro Gly Trp
1               5

<210> SEQ ID NO 36
<211> LENGTH: 9
<212> TYPE: PRT
<213> ORGANISM: Artificial Sequence
<220> FEATURE:
<223> OTHER INFORMATION: Peptide mimotope

<400> SEQUENCE: 36

Cys Gln Pro Ala Tyr Tyr His Thr Cys
1               5

<210> SEQ ID NO 37
<211> LENGTH: 9
<212> TYPE: PRT
<213> ORGANISM: Artificial Sequence
<220> FEATURE:
<223> OTHER INFORMATION: Peptide mimotope

<400> SEQUENCE: 37

Cys His Leu Gly Tyr Pro Gly Arg Cys
1               5

<210> SEQ ID NO 38
<211> LENGTH: 9
<212> TYPE: PRT
<213> ORGANISM: Artificial Sequence
<220> FEATURE:
<223> OTHER INFORMATION: Peptide mimotope

<400> SEQUENCE: 38

Cys His Tyr Gly Tyr Pro Gly Arg Cys
1               5

<210> SEQ ID NO 39
<211> LENGTH: 9
<212> TYPE: PRT
<213> ORGANISM: Artificial Sequence
<220> FEATURE:
<223> OTHER INFORMATION: Peptide mimotope

<400> SEQUENCE: 39

Cys His Leu Gly Tyr Pro Gly Trp Cys
1               5

<210> SEQ ID NO 40
<211> LENGTH: 9
<212> TYPE: PRT
<213> ORGANISM: Artificial Sequence
<220> FEATURE:
<223> OTHER INFORMATION: Peptide mimotope

<400> SEQUENCE: 40

Cys His Tyr Ser Tyr Pro Gly Val Cys
1               5
```

```
<210> SEQ ID NO 41
<211> LENGTH: 9
<212> TYPE: PRT
<213> ORGANISM: Artificial Sequence
<220> FEATURE:
<223> OTHER INFORMATION: Peptide mimotope

<400> SEQUENCE: 41

Cys His Tyr Gly Tyr Pro Gly Val Cys
1               5

<210> SEQ ID NO 42
<211> LENGTH: 9
<212> TYPE: PRT
<213> ORGANISM: Artificial Sequence
<220> FEATURE:
<223> OTHER INFORMATION: Peptide mimotope

<400> SEQUENCE: 42

Cys His Tyr Ser Tyr Pro Gly Trp Cys
1               5

<210> SEQ ID NO 43
<211> LENGTH: 9
<212> TYPE: PRT
<213> ORGANISM: Artificial Sequence
<220> FEATURE:
<223> OTHER INFORMATION: Peptide mimotope

<400> SEQUENCE: 43

Cys His Leu Arg Tyr Pro Gly Glu Cys
1               5

<210> SEQ ID NO 44
<211> LENGTH: 9
<212> TYPE: PRT
<213> ORGANISM: Artificial Sequence
<220> FEATURE:
<223> OTHER INFORMATION: Peptide mimotope

<400> SEQUENCE: 44

Cys His Tyr Arg Tyr Pro Gly Glu Cys
1               5

<210> SEQ ID NO 45
<211> LENGTH: 9
<212> TYPE: PRT
<213> ORGANISM: Artificial Sequence
<220> FEATURE:
<223> OTHER INFORMATION: Peptide mimotope

<400> SEQUENCE: 45

Cys His Leu Asn Tyr Pro Gly Tyr Cys
1               5

<210> SEQ ID NO 46
<211> LENGTH: 9
<212> TYPE: PRT
<213> ORGANISM: Artificial Sequence
<220> FEATURE:
<223> OTHER INFORMATION: Peptide mimotope

<400> SEQUENCE: 46

Cys His Leu Gly Tyr Pro Gly Tyr Cys
1               5

<210> SEQ ID NO 47
```

```
<211> LENGTH: 9
<212> TYPE: PRT
<213> ORGANISM: Artificial Sequence
<220> FEATURE:
<223> OTHER INFORMATION: Peptide mimotope

<400> SEQUENCE: 47

Cys His Leu Asn Tyr Pro Gly Trp Cys
1               5

<210> SEQ ID NO 48
<211> LENGTH: 9
<212> TYPE: PRT
<213> ORGANISM: Artificial Sequence
<220> FEATURE:
<223> OTHER INFORMATION: Peptide mimotope

<400> SEQUENCE: 48

Cys Tyr Lys Gly Tyr Pro Gly Tyr Cys
1               5

<210> SEQ ID NO 49
<211> LENGTH: 9
<212> TYPE: PRT
<213> ORGANISM: Artificial Sequence
<220> FEATURE:
<223> OTHER INFORMATION: Peptide mimotope

<400> SEQUENCE: 49

Cys His Tyr Gly Tyr Pro Gly Trp Cys
1               5

<210> SEQ ID NO 50
<211> LENGTH: 11
<212> TYPE: PRT
<213> ORGANISM: Artificial Sequence
<220> FEATURE:
<223> OTHER INFORMATION: Peptide mimotope

<400> SEQUENCE: 50

Ala Cys Gln Pro Ala Tyr Tyr His Thr Cys Gly
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Peptide mimotope

<400> SEQUENCE: 51

Ala Cys His Leu Gly Tyr Pro Gly Arg Cys Gly
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Peptide mimotope

<400> SEQUENCE: 52

Ala Cys His Tyr Gly Tyr Pro Gly Arg Cys Gly
1               5                   10

<210> SEQ ID NO 53
<211> LENGTH: 11
```

```
<212> TYPE: PRT
<213> ORGANISM: Artificial Sequence
<220> FEATURE:
<223> OTHER INFORMATION: Peptide mimotope

<400> SEQUENCE: 53

Ala Cys His Leu Gly Tyr Pro Gly Trp Cys Gly
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Peptide mimotope

<400> SEQUENCE: 54

Ala Cys His Tyr Ser Tyr Pro Gly Val Cys Gly
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Peptide mimotope

<400> SEQUENCE: 55

Ala Cys His Tyr Gly Tyr Pro Gly Val Cys Gly
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Peptide mimotope

<400> SEQUENCE: 56

Ala Cys His Tyr Ser Tyr Pro Gly Trp Cys Gly
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Peptide mimotope

<400> SEQUENCE: 57

Ala Cys His Leu Arg Tyr Pro Gly Glu Cys Gly
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Peptide mimotope

<400> SEQUENCE: 58

Ala Cys His Tyr Arg Tyr Pro Gly Glu Cys Gly
1               5                   10

<210> SEQ ID NO 59
<211> LENGTH: 11
<212> TYPE: PRT
```

<213> ORGANISM: Artificial Sequence
<220> FEATURE:
<223> OTHER INFORMATION: Peptide mimotope

<400> SEQUENCE: 59

Ala Cys His Leu Asn Tyr Pro Gly Tyr Cys Gly
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Peptide mimotope

<400> SEQUENCE: 60

Ala Cys His Leu Gly Tyr Pro Gly Tyr Cys Gly
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Peptide mimotope

<400> SEQUENCE: 61

Ala Cys His Leu Asn Tyr Pro Gly Trp Cys Gly
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Peptide mimotope

<400> SEQUENCE: 62

Ala Cys Tyr Lys Gly Tyr Pro Gly Tyr Cys Gly
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Peptide mimotope

<400> SEQUENCE: 63

Ala Cys His Tyr Gly Tyr Pro Gly Trp Cys Gly
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Peptide mimotope

<400> SEQUENCE: 64

Tyr Leu His Pro Asp
1               5

<210> SEQ ID NO 65
<211> LENGTH: 12
<212> TYPE: PRT
<213> ORGANISM: Artificial Sequence

```
<220> FEATURE:
<223> OTHER INFORMATION: Peptide mimotope

<400> SEQUENCE: 65

Thr Pro Tyr His His Pro Asp Phe Pro Tyr Trp Phe
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Peptide mimotope

<400> SEQUENCE: 66

Tyr Leu His Pro Asp Tyr Pro
1               5

<210> SEQ ID NO 67
<211> LENGTH: 7
<212> TYPE: PRT
<213> ORGANISM: Artificial Sequence
<220> FEATURE:
<223> OTHER INFORMATION: Peptide mimotope

<400> SEQUENCE: 67

Tyr Leu His Pro Asp Val Met
1               5

<210> SEQ ID NO 68
<211> LENGTH: 35
<212> TYPE: PRT
<213> ORGANISM: Artificial Sequence
<220> FEATURE:
<223> OTHER INFORMATION: Peptide mimotope

<400> SEQUENCE: 68

Pro Arg Cys Lys Ser Glu Gly Pro His His Pro Asp Tyr Pro Asp Cys
1               5                   10                  15

Arg Arg Asp Ser Asp Cys Asn Gly Glu Cys Ile Cys Arg Gly Asn Gly
            20                  25                  30

Tyr Cys Gly
        35

<210> SEQ ID NO 69
<211> LENGTH: 10
<212> TYPE: PRT
<213> ORGANISM: Artificial Sequence
<220> FEATURE:
<223> OTHER INFORMATION: Peptide mimotope

<400> SEQUENCE: 69

Ala Cys Arg His Pro Asp His Leu Asp Cys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Peptide mimotope

<400> SEQUENCE: 70

Ala Cys His Glu Thr His His Pro Asp Cys
1               5                   10
```

```
<210> SEQ ID NO 71
<211> LENGTH: 12
<212> TYPE: PRT
<213> ORGANISM: Artificial Sequence
<220> FEATURE:
<223> OTHER INFORMATION: Peptide mimotope

<400> SEQUENCE: 71

Ser Phe Arg Asp Met Asn Tyr Ser Asp Tyr Phe Met
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Peptide mimotope

<400> SEQUENCE: 72

His Ile Leu Pro Leu Tyr Pro
1               5

<210> SEQ ID NO 73
<211> LENGTH: 7
<212> TYPE: PRT
<213> ORGANISM: Artificial Sequence
<220> FEATURE:
<223> OTHER INFORMATION: Peptide mimotope

<400> SEQUENCE: 73

Ser Pro Tyr Met Pro Met Gln
1               5

<210> SEQ ID NO 74
<211> LENGTH: 17
<212> TYPE: PRT
<213> ORGANISM: Artificial Sequence
<220> FEATURE:
<223> OTHER INFORMATION: Peptide mimotope

<400> SEQUENCE: 74

Asp Arg Cys Trp Leu Glu Gln Trp Pro Cys Arg Asp Ser Asp Ile
1               5                   10                  15

Pro

<210> SEQ ID NO 75
<211> LENGTH: 35
<212> TYPE: PRT
<213> ORGANISM: Artificial Sequence
<220> FEATURE:
<223> OTHER INFORMATION: Peptide mimotope

<400> SEQUENCE: 75

Gln Thr Cys Asp His Asp Thr Arg His Pro Thr Gly Asp Asp Leu Cys
1               5                   10                  15

Arg Arg Asp Ser Asp Cys Gly Gly Asn Cys Ile Cys Arg Gly Asn Gly
            20                  25                  30

Tyr Cys Gly
        35

<210> SEQ ID NO 76
<211> LENGTH: 14
<212> TYPE: PRT
<213> ORGANISM: Artificial Sequence
<220> FEATURE:
```

```
<223> OTHER INFORMATION: Peptide mimotope

<400> SEQUENCE: 76

Ala Cys His Leu Gly Tyr Pro Gly Arg Cys Gly Gly Gly Ser
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Peptide mimotope

<400> SEQUENCE: 77

Ala Cys His Tyr Ser Tyr Pro Gly Val Cys Gly Gly Gly Ser
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Peptide mimotope

<400> SEQUENCE: 78

Ala Cys His Leu Asn Tyr Pro Gly Tyr Cys Gly Gly Gly Ser
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Peptide mimotope

<400> SEQUENCE: 79

Ala Cys His Leu Arg Tyr Pro Gly Glu Cys Gly Gly Gly Ser
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Peptide mimotope

<400> SEQUENCE: 80

Ala Cys Tyr Lys Gly Tyr Pro Gly Tyr Cys Gly Gly Gly Ser
1               5                   10
```

PEPTIDE MIMOTOPES OF CLAUDIN 18.2 AND USES THEREOF

CROSS-REFERENCE TO RELATED APPLICATIONS

This application is a national stage entry of international application PCT/EP2014/000244, filed on Jan. 29, 2014, the entire contents of which are incorporated herein by reference.

The present invention provides molecules that mimic antigenic determinants of the integral transmembrane protein claudin 18.2 (CLDN18.2). These molecules compete with CLDN18.2 for binding to a CLDN18.2 binding domain, e.g. a CLDN18.2 binding domain of an antibody, and are capable of detecting antibodies against CLDN18.2. The mimotopes of the invention may be used to generate or inhibit immune responses in animals and preferably humans. Additionally, they may serve as tools for the detection of anti CLDN18.2 antibodies, CLDN18.2 binding domains or alternative antibody formats in biological samples as well as for purification purposes of said molecules.

Claudins are integral membrane proteins located within the tight junctions of epithelia and endothelia. Claudins are predicted to have four transmembrane segments with two extracellular loops, and N- and C-termini located in the cytoplasm. The claudin (CLDN) family of transmembrane proteins plays a critical role in the maintenance of epithelial and endothelial tight junctions and might also play a role in the maintenance of the cytoskeleton and in cell signalling.

The claudin 18 (CLDN18) molecule is an integral transmembrane protein (tetraspanin) having four membrane spanning hydrophobic regions and two extracellular loops (loop1 embraced by hydrophobic region 1 and hydrophobic region 2; loop2 embraced by hydrophobic regions 3 and 4). CLDN18 exists in two different splice variants, which are described in mouse and in human (Niimi, Mol. Cell. Biol. 21:7380-90, 2001). The splice variants (Genbank accession number: splice variant 1 (CLDN18.1): NP 057453, NM 016369, and splice variant 2 (CLDN18.2): NM_001002026, NP_001002026) have a molecular weight of approximately 27.9/27.72 kD. The splice variants CLDN18.1 and CLDN18.2 differ in the N-terminal portion which comprises the first transmembrane (TM) region and loop1, whereas the primary protein sequence of the C-terminus is identical.

In normal tissues, there is no detectable expression of CLDN18.2 with exception of stomach where CLDN18.2 is expressed exclusively on short-lived differentiated gastric epithelial cells. CLDN18.2 is maintained in the course of malignant transformation and thus frequently displayed on the surface of human gastric cancer cells. Moreover, this pan-tumoral antigen is ectopically activated at significant levels in esophageal, pancreatic and lung adenocarcinomas. The CLDN18.2 protein is also localized in lymph node metastases of gastric cancer adenocarcinomas and in distant metastases especially into the ovary (so-called Krukenberg tumors).

IMAB362 is a highly tumor-specific monoclonal IgG1 antibody currently in clinical development among others for the treatment of advanced gastro-esophageal and stomach cancer [Sahin, U. et al., Clin. Cancer Res. 2008, 14, 7624-7634; Woll, S. et al., Int. J. Cancer 2013, DOI: 10.1002/ijc.28400]. The antibody is directed against the cancer specific cell surface target Claudin 18 isoform 2 (CLDN18.2). A phase I and a phase IIa trial have been conducted in multiply pre-treated late-stage patients with advanced gastro-esophageal cancer using IMAB362 as single agent and have shown tolerability and antitumoral activity. In an on-going randomized Phase IIb trial, IMAB362 is combined with standard chemotherapy for first-line treatment of gastro-esophageal cancer [Schuler, M. H. et al., J. Clin. Oncol. 2013, 31 (suppl; abstr 4080)].

For the development of IMAB362 towards clinical use the detection and quantification of the antibody after application to animals and patients is crucial for the characterization of ADME and PK properties. Typically, ELISA-based assays are being applied for this purpose using the corresponding antigen. Unfortunately, transmembrane proteins are often difficult to produce and handle due to their peculiar nature as membrane-embedded structures [Scott, D. J. et al., Curr. Opin. Chem. Biol. 2013, 17, 427-435]. This obstacle can be overcome by using anti-idiotypic antibodies which bind specifically to the antigen binding region of the therapeutic antibody. However, generating such anti-idiotypic antibodies is time-consuming and expensive. Therefore, mimotopes as easier-to-prepare structures are considered useful substitutes to mimic the full-length antigen, allowing tight specific binding of the therapeutic antibody. Mimotopes can be proteins but also oligopeptides [Casey, J. L. et al., J. Clin. Microbiol. 2006, 44, 764-771; Kieber-Emmons, T., Immunol. Res. 1998, 17, 95-108; Tang, Y., et al., J. Biol. Chem. 1999, 274, 27371-27378; Wagner, S. et al., Clin. Cancer Res. 2008, 14, 8178-8183].

As an alternative to protein ELISA, peptide ELISA is a technique that is increasingly being used [Velumani, S. et al., PLoS. One 2011, DOI: 10.1371/journal.pone.0020737]. Peptides are easily accessible by chemical synthesis, show higher stability and are easier to handle compared to proteins. In general, peptide ELISA enables the analysis of protein/protein interactions on the amino acid sequence level, e.g. for definition of protein interaction sites. Specifically binding peptides—or peptide-based mimotopes—for peptide ELISA can be discovered with several approaches which can be either knowledge-based or based on random library approaches. Phage display is a well-established technique for screening large protein or peptide libraries that often yield strong binding partners for disease-related proteins or antibodies [Molek, P. et al., Molecules 2011, 16, 857-887; Szardenings, M., Transduct. Res. 2003, 23, 307-349]. However, in some cases the affinities or physicochemical properties of these hit peptides need to be optimized. Here, peptide microarrays offer an efficient approach. Thousands of peptides can be screened economically in parallel requiring only small amounts of precious analyte. In addition, assays on peptide microarrays can be set up rapidly because the read-out is frequently achieved by standardized fluorescence-based methods allowing low background when glass surfaces are being used [Lorenz, P. et al., Methods Mol. Biol. 2009, 524, 247-258; Nahtman, T. et al., J. Immunol. Methods 2007, 328, 1-13; Thiele, A. et al., Methods Mol. Biol. 2009, 570, 19-65; Pai, J. et al., J. Am. Chem. Soc. 2012, 134, 19287-19296].

It has been an object of the invention to prepare structures which may serve as substitutes to mimic the full-length CLDN18.2 antigen and which are available in a format which is compatible with biochemical formats for assay analytics and purification procedures.

According to the invention, the systematic development of peptide-based mimotopes for CLDN18.2 which bind to the drug candidate IMAB362 is reported. The mimotope discovery and optimization process was performed via a combined screening and affinity maturation approach using phage display followed by a peptide-microarray-based characterization of the structure-activity-relationship (SAR) of the peptide hits leading to rapid optimization of their binding properties. The resulting mimotopes were shown to bind strongly and specifically and to be well-suited for detection of the antibody in human and murine serum.

The identification and isolation of molecules that mimic antigenic determinants of CLDN18.2 provides significant advantages and benefits. The use of molecules mimicking epitopes, and in particular peptide based mimotopes, as diagnostic antigens is advantageous because it allows focus on relevant single specificities and avoids the diagnostically unimportant epitopes present in complex antigens. Peptides of high quality and stability can be cheaply and reproducibly produced and are easily applied to ELISA as well as other formats.

SUMMARY OF THE INVENTION

The present invention provides a peptide mimotope of claudin 18.2 (CLDN18.2). In one embodiment, the peptide mimotope is a structural mimic of either a linear or conformational CLDN18.2 epitope. In one embodiment, the peptide mimotope is a structural mimic of an epitope in the extracellular domain of CLDN18.2.

In one embodiment, the peptide mimotope has a binding capacity to a CLDN18.2 binding domain and/or competes with CLDN18.2 for binding to a CLDN18.2 binding domain. In one embodiment, the CLDN18.2 binding domain is comprised by a binding agent to CLDN18.2. In one embodiment, the binding agent to CLDN18.2 is selected from the group consisting of an antibody or antibody fragment to CLDN18.2, a bispecific or multispecific molecule comprising a binding domain to CLDN18.2 and a chimeric antigen receptor (CAR). In one embodiment, the binding agent to CLDN18.2 is selected from the group consisting of artificial binding molecules (scaffolds) including but not limited to nanobodies, affibodies, anticalins, DARPins, monobodies, avimers, and microbodies. In one embodiment, the bispecific molecule is a bispecific antibody. In one embodiment, the bispecific antibody is a bispecific single chain antibody. In one embodiment, the binding agent binds to an epitope in the extracellular domain of CLDN18.2. In one embodiment, said binding is a specific binding.

In one embodiment, the bispecific or multispecific molecule comprises a first binding domain binding to CLDN18.2 and a second binding domain binding to a T cell. In one embodiment, the bispecific or multispecific molecule comprises a first binding domain binding to CLDN18.2 and a second binding domain binding to CD3. In one embodiment, said second binding domain binding to CD3 binds to the epsilon-chain of CD3. In one embodiment, said CD3 is expressed on the surface of a T cell. In one embodiment, binding of said binding agent to CD3 on T cells results in proliferation and/or activation of said T cells, wherein said activated T cells preferably release cytotoxic factors, e.g. perforins and granzymes, and initiate cytolysis and apoptosis of cancer cells.

In one embodiment, the CLDN18.2 binding domain comprises a variable domain of a heavy chain of an immunoglobulin (VH) with a specificity for CLDN18.2 (VH (CLDN18.2)) and a variable domain of a light chain of an immunoglobulin (VL) with a specificity for CLDN18.2 (VH(CLDN18.2)). In one embodiment, said VH(CLDN18.2) comprises an amino acid sequence represented by SEQ ID NO: 2 or a fragment thereof or a variant of said amino acid sequence or fragment and the VL(CLDN18.2) comprises an amino acid sequence represented by SEQ ID NO: 3 or a fragment thereof or a variant of said amino acid sequence or fragment.

In one embodiment, the peptide mimotope of the present invention comprises the amino acid sequence Xaa1 Xaa2 Xaa3 Tyr Xaa4 Xaa5 Xaa6   (SEQ ID NO: 14)

wherein
Xaa1 is any amino acid, preferably an amino acid selected from the group consisting of Gln, His, Tyr, Lys and Met, more preferably an amino acid selected from the group consisting of Gln, His and Tyr,
Xaa2 is any amino acid, preferably an amino acid selected from the group consisting of Pro, Leu, Lys, Tyr, Phe and Arg, more preferably an amino acid selected from the group consisting of Pro, Leu, Lys and Tyr,
Xaa3 is any amino acid, preferably an amino acid selected from the group consisting of Ala, Gly, Asn, Arg, Ser, Lys, Trp, Phe and Tyr, more preferably an amino acid selected from the group consisting of Ala, Gly, Asn, Arg and Ser,
Xaa4 is any amino acid, preferably an amino acid selected from the group consisting of Tyr, Pro and Arg, more preferably an amino acid selected from the group consisting of Tyr and Pro,
Xaa5 is any amino acid, preferably an amino acid selected from the group consisting of His, Gly, Lys and Arg, more preferably an amino acid selected from the group consisting of His and Gly, and
Xaa6 is any amino acid, preferably an amino acid selected from the group consisting of Thr, Trp, Tyr, Glu, Arg, Val, Ile, Leu, Met, Ala, Phe and Lys, more preferably an amino acid selected from the group consisting of Thr, Trp, Tyr, Glu, Arg and Val.

In one embodiment, the peptide mimotope of the present invention comprises the amino acid sequence Cys Xaa1 Xaa2 Xaa3 Tyr Xaa4 Xaa5 Xaa6 Cys   (SEQ ID NO: 15)

wherein
Xaa1 is any amino acid, preferably an amino acid selected from the group consisting of Gln, His, Tyr, Lys and Met, more preferably an amino acid selected from the group consisting of Gln, His and Tyr,
Xaa2 is any amino acid, preferably an amino acid selected from the group consisting of Pro, Leu, Lys, Tyr, Phe and Arg, more preferably an amino acid selected from the group consisting of Pro, Leu, Lys and Tyr,
Xaa3 is any amino acid, preferably an amino acid selected from the group consisting of Ala, Gly, Asn, Arg, Ser, Lys, Trp, Phe and Tyr, more preferably an amino acid selected from the group consisting of Ala, Gly, Asn, Arg and Ser,
Xaa4 is any amino acid, preferably an amino acid selected from the group consisting of Tyr, Pro and Arg, more preferably an amino acid selected from the group consisting of Tyr and Pro,
Xaa5 is any amino acid, preferably an amino acid selected from the group consisting of His, Gly, Lys and Arg, more preferably an amino acid selected from the group consisting of His and Gly, and
Xaa6 is any amino acid, preferably an amino acid selected from the group consisting of Thr, Trp, Tyr, Glu, Arg, Val, Ile, Leu, Met, Ala, Phe and Lys, more preferably an amino acid selected from the group consisting of Thr, Trp, Tyr, Glu, Arg and Val.

In one embodiment, the peptide mimotope of the present invention comprises the amino acid sequence Ala Cys Xaa1 Xaa2 Xaa3 Tyr Xaa4
        Xaa5 Xaa6 Cys                          (SEQ ID NO: 16)

wherein
Xaa1 is any amino acid, preferably an amino acid selected from the group consisting of Gln, His, Tyr, Lys and Met, more preferably an amino acid selected from the group consisting of Gln, His and Tyr,
Xaa2 is any amino acid, preferably an amino acid selected from the group consisting of Pro, Leu, Lys, Tyr, Phe and Arg, more preferably an amino acid selected from the group consisting of Pro, Leu, Lys and Tyr,
Xaa3 is any amino acid, preferably an amino acid selected from the group consisting of Ala, Gly, Asn, Arg, Ser, Lys, Trp, Phe and Tyr, more preferably an amino acid selected from the group consisting of Ala, Gly, Asn, Arg and Ser,
Xaa4 is any amino acid, preferably an amino acid selected from the group consisting of Tyr, Pro and Arg, more preferably an amino acid selected from the group consisting of Tyr and Pro,
Xaa5 is any amino acid, preferably an amino acid selected from the group consisting of His, Gly, Lys and Arg, more preferably an amino acid selected from the group consisting of His and Gly, and
Xaa6 is any amino acid, preferably an amino acid selected from the group consisting of Thr, Trp, Tyr, Glu, Arg, Val, Ile, Leu, Met, Ala, Phe and Lys, more preferably an amino acid selected from the group consisting of Thr, Trp, Tyr, Glu, Arg and Val.

In one embodiment, the peptide mimotope of the present invention comprises the amino acid sequence Ala Cys Xaa1 Xaa2 Xaa3 Tyr Xaa4 Xaa5 Xaa6 Cys
        Gly                                    (SEQ ID NO: 17)

wherein
Xaa1 is any amino acid, preferably an amino acid selected from the group consisting of Gln, His, Tyr, Lys and Met, more preferably an amino acid selected from the group consisting of Gln, His and Tyr,
Xaa2 is any amino acid, preferably an amino acid selected from the group consisting of Pro, Leu, Lys, Tyr, Phe and Arg, more preferably an amino acid selected from the group consisting of Pro, Leu, Lys and Tyr,
Xaa3 is any amino acid, preferably an amino acid selected from the group consisting of Ala, Gly, Asn, Arg, Ser, Lys, Trp, Phe and Tyr, more preferably an amino acid selected from the group consisting of Ala, Gly, Asn, Arg and Ser,
Xaa4 is any amino acid, preferably an amino acid selected from the group consisting of Tyr, Pro and Arg, more preferably an amino acid selected from the group consisting of Tyr and Pro,
Xaa5 is any amino acid, preferably an amino acid selected from the group consisting of His, Gly, Lys and Arg, more preferably an amino acid selected from the group consisting of His and Gly, and
Xaa6 is any amino acid, preferably an amino acid selected from the group consisting of Thr, Trp, Tyr, Glu, Arg, Val, Ile, Leu, Met, Ala, Phe and Lys, more preferably an amino acid selected from the group consisting of Thr, Trp, Tyr, Glu, Arg and Val.

In one embodiment, the peptide mimotope of the present invention comprises the amino acid sequence Tyr Pro Gly.

In one embodiment, the peptide mimotope of the present invention comprises the amino acid sequence Xaa1 Xaa2 Xaa3 Tyr Pro Gly Xaa4           (SEQ ID NO: 18)

wherein
Xaa1 is any amino acid, preferably an amino acid selected from the group consisting of Gln, His, Tyr, Lys and Met, more preferably an amino acid selected from the group consisting of His and Tyr,
Xaa2 is any amino acid, preferably an amino acid selected from the group consisting of Pro, Leu, Lys, Tyr, Phe and Arg, more preferably an amino acid selected from the group consisting of Leu, Lys, Tyr and Phe, more preferably an amino acid selected from the group consisting of Leu, Lys and Tyr,
Xaa3 is any amino acid, preferably an amino acid selected from the group consisting of Ala, Gly, Asn, Arg, Ser, Lys, Trp, Phe and Tyr, more preferably an amino acid selected from the group consisting of Gly, Asn, Arg, Ser, Trp and Lys, more preferably an amino acid selected from the group consisting of Gly, Asn, Arg and Ser, and
Xaa4 is any amino acid, preferably an amino acid selected from the group consisting of Thr, Trp, Tyr, Glu, Arg, Val, Ile, Leu, Met, Ala, Phe and Lys, more preferably an amino acid selected from the group consisting of Trp, Tyr, Glu, Arg, Val, Lys, Ile, Met and Phe, more preferably an amino acid selected from the group consisting of Trp, Tyr, Glu, Arg and Val.

In one embodiment, the peptide mimotope of the present invention comprises the amino acid sequence Cys Xaa1 Xaa2 Xaa3 Tyr Pro Gly Xaa4 Cys   (SEQ ID NO: 19)

wherein
Xaa1 is any amino acid, preferably an amino acid selected from the group consisting of Gln, His, Tyr, Lys and Met, more preferably an amino acid selected from the group consisting of His and Tyr,
Xaa2 is any amino acid, preferably an amino acid selected from the group consisting of Pro, Leu, Lys, Tyr, Phe and Arg, more preferably an amino acid selected from the group consisting of Leu, Lys, Tyr and Phe, more preferably an amino acid selected from the group consisting of Leu, Lys and Tyr,
Xaa3 is any amino acid, preferably an amino acid selected from the group consisting of Ala, Gly, Asn, Arg, Ser, Lys, Trp, Phe and Tyr, more preferably an amino acid selected from the group consisting of Gly, Asn, Arg, Ser, Trp and Lys, more preferably an amino acid selected from the group consisting of Gly, Asn, Arg and Ser, and
Xaa4 is any amino acid, preferably an amino acid selected from the group consisting of Thr, Trp, Tyr, Glu, Arg, Val, Ile, Leu, Met, Ala, Phe and Lys, more preferably an amino acid selected from the group consisting of Trp, Tyr, Glu, Arg, Val, Lys, Ile, Met and Phe, more preferably an amino acid selected from the group consisting of Trp, Tyr, Glu, Arg and Val.

In one embodiment, the peptide mimotope of the present invention comprises the amino acid sequence Ala Cys Xaa1 Xaa2 Xaa3 Tyr Pro Gly Xaa4 Cys   (SEQ ID NO: 20)

wherein
Xaa1 is any amino acid, preferably an amino acid selected from the group consisting of Gln, His, Tyr, Lys and Met, more preferably an amino acid selected from the group consisting of His and Tyr,
Xaa2 is any amino acid, preferably an amino acid selected from the group consisting of Pro, Leu, Lys, Tyr, Phe and Arg, more preferably an amino acid selected from the group consisting of Leu, Lys, Tyr and Phe, more preferably an amino acid selected from the group consisting of Leu, Lys and Tyr, Xaa3 is any amino acid, preferably an amino acid selected from the group consisting of Ala, Gly, Asn, Arg, Ser, Lys, Trp, Phe and Tyr, more preferably an amino acid selected from the group consisting of Gly, Asn, Arg, Ser, Trp and Lys, more preferably an amino acid selected from the group consisting of Gly, Asn, Arg and Ser, and Xaa4 is any amino acid, preferably an amino acid selected from the group consisting of Thr, Trp, Tyr, Glu, Arg, Val, Ile, Leu, Met, Ala, Phe and Lys, more preferably an amino acid selected from the group consisting of Trp, Tyr, Glu, Arg, Val, Lys, Ile, Met and Phe, more preferably an amino acid selected from the group consisting of Trp, Tyr, Glu, Arg and Val.

In one embodiment, the peptide mimotope of the present invention comprises the amino acid sequence Ala Cys Xaa1 Xaa2 Xaa3 Tyr Pro Gly Xaa4 Cys Gly (SEQ ID NO: 21)

wherein

Xaa1 is any amino acid, preferably an amino acid selected from the group consisting of Gln, His, Tyr, Lys and Met, more preferably an amino acid selected from the group consisting of His and Tyr, Xaa2 is any amino acid, preferably an amino acid selected from the group consisting of Pro, Leu, Lys, Tyr, Phe and Arg, more preferably an amino acid selected from the group consisting of Leu, Lys, Tyr and Phe, more preferably an amino acid selected from the group consisting of Leu, Lys and Tyr, Xaa3 is any amino acid, preferably an amino acid selected from the group consisting of Ala, Gly, Asn, Arg, Ser, Lys, Trp, Phe and Tyr, more preferably an amino acid selected from the group consisting of Gly, Asn, Arg, Ser, Trp and Lys, more preferably an amino acid selected from the group consisting of Gly, Asn, Arg and Ser, and Xaa4 is any amino acid, preferably an amino acid selected from the group consisting of Thr, Trp, Tyr, Glu, Arg, Val, Ile, Leu, Met, Ala, Phe and Lys, more preferably an amino acid selected from the group consisting of Trp, Tyr, Glu, Arg, Val, Lys, Ile, Met and Phe, more preferably an amino acid selected from the group consisting of Trp, Tyr, Glu, Arg and Val.

In one embodiment, the peptide mimotope of the present invention comprises an amino acid sequence selected from the group consisting of:

| | |
|---|---|
| Gln Pro Ala Tyr Tyr His Thr | (SEQ ID NO: 22), |
| His Leu Gly Tyr Pro Gly Arg | (SEQ ID NO: 23), |
| His Tyr Gly Tyr Pro Gly Arg | (SEQ ID NO: 24), |
| His Leu Gly Tyr Pro Gly Trp | (SEQ ID NO: 25), |
| His Tyr Ser Tyr Pro Gly Val | (SEQ ID NO: 26), |
| His Tyr Gly Tyr Pro Gly Val | (SEQ ID NO: 27), |
| His Tyr Ser Tyr Pro Gly Trp | (SEQ ID NO: 28), |
| His Leu Arg Tyr Pro Gly Glu | (SEQ ID NO: 29), |
| His Tyr Arg Tyr Pro Gly Glu | (SEQ ID NO: 30), |
| His Leu Asn Tyr Pro Gly Tyr | (SEQ ID NO: 31), |
| His Leu Gly Tyr Pro Gly Tyr | (SEQ ID NO: 32), |
| His Leu Asn Tyr Pro Gly Trp | (SEQ ID NO: 33), |
| Tyr Lys Gly Tyr Pro Gly Tyr | (SEQ ID NO: 34), |
| His Tyr Gly Tyr Pro Gly Trp | (SEQ ID NO: 35), and | a fragment of said amino acid sequence or a variant of said amino acid sequence or fragment.

In one embodiment, the peptide mimotope of the present invention comprises an amino acid sequence selected from the group consisting of:

| | |
|---|---|
| Cys Gln Pro Ala Tyr Tyr His Thr Cys | (SEQ ID NO: 36), |
| Cys His Leu Gly Tyr Pro Gly Arg Cys | (SEQ ID NO: 37), |
| Cys His Tyr Gly Tyr Pro Gly Arg Cys | (SEQ ID NO: 38), |
| Cys His Leu Gly Tyr Pro Gly Trp Cys | (SEQ ID NO: 39), |
| Cys His Tyr Ser Tyr Pro Gly Val Cys | (SEQ ID NO: 40), |
| Cys His Tyr Gly Tyr Pro Gly Val Cys | (SEQ ID NO: 41), |
| Cys His Tyr Ser Tyr Pro Gly Trp Cys | (SEQ ID NO: 42), |
| Cys His Leu Arg Tyr Pro Gly Glu Cys | (SEQ ID NO: 43), |
| Cys His Tyr Arg Tyr Pro Gly Glu Cys | (SEQ ID NO: 44), |
| Cys His Leu Asn Tyr Pro Gly Tyr Cys | (SEQ ID NO: 45), |
| Cys His Leu Gly Tyr Pro Gly Tyr Cys | (SEQ ID NO: 46), |
| Cys His Leu Asn Tyr Pro Gly Trp Cys | (SEQ ID NO: 47), |
| Cys Tyr Lys Gly Tyr Pro Gly Tyr Cys | (SEQ ID NO: 48), |
| Cys His Tyr Gly Tyr Pro Gly Trp Cys | (SEQ ID NO: 49), and | a fragment of said amino acid sequence or a variant of said amino acid sequence or fragment.

In one embodiment, the peptide mimotope of the present invention comprises an amino acid sequence selected from the group consisting of:

| | |
|---|---|
| Ala Cys Gln Pro Ala Tyr Tyr His Thr Cys Gly | (SEQ ID NO: 50), |
| Ala Cys His Leu Gly Tyr Pro Gly Arg Cys Gly | (SEQ ID NO: 51), |
| Ala Cys His Tyr Gly Tyr Pro Gly Arg Cys Gly | (SEQ ID NO: 52), |
| Ala Cys His Leu Gly Tyr Pro Gly Trp Cys Gly | (SEQ ID NO: 53), |
| Ala Cys His Tyr Ser Tyr Pro Gly Val Cys Gly | (SEQ ID NO: 54), |
| Ala Cys His Tyr Gly Tyr Pro Gly Val Cys Gly | (SEQ ID NO: 55), |
| Ala Cys His Tyr Ser Tyr Pro Gly Trp Cys Gly | (SEQ ID NO: 56, |
| Ala Cys His Leu Arg Tyr Pro Gly Glu Cys Gly | (SEQ ID NO: 57), |
| Ala Cys His Tyr Arg Tyr Pro Gly Glu Cys Gly | (SEQ ID NO: 58), |
| Ala Cys His Leu Asn Tyr Pro Gly Tyr Cys Gly | (SEQ ID NO: 59), |
| Ala Cys His Leu Gly Tyr Pro Gly Tyr Cys Gly | (SEQ ID NO: 60), |
| Ala Cys His Leu Asn Tyr Pro Gly Trp Cys Gly | (SEQ ID NO: 61), |
| Ala Cys Tyr Lys Gly Tyr Pro Gly Tyr Cys Gly | (SEQ ID NO: 62), |
| Ala Cys His Tyr Gly Tyr Pro Gly Trp Cys Gly | (SEQ ID NO: 63), and | a fragment of said amino acid sequence or a variant of said amino acid sequence or fragment.

In one embodiment, the peptide mimotope of the present invention comprises the amino acid sequence His Pro Asp. In one embodiment, the peptide mimotope of the present invention comprises the amino acid sequence Tyr Leu His Pro Asp (SEQ ID NO: 64).

In one embodiment, the peptide mimotope of the present invention comprises an amino acid sequence selected from the group consisting of:

| | |
|---|---|
| Thr Pro Tyr His His Pro Asp Phe Pro Tyr Trp Phe | (SEQ ID NO: 65), |
| Tyr Leu His Pro Asp Tyr Pro | (SEQ ID NO: 66), |
| Tyr Leu His Pro Asp Val Met | (SEQ ID NO: 67), |
| Pro Arg Cys Lys Ser Glu Gly Pro His His Pro Asp Tyr Pro Asp Cys Arg Arg Asp Ser Asp Cys Asn Gly Glu Cys Ile Cys Arg Gly Asn Gly Tyr Cys Gly | (SEQ ID NO: 68), |
| Ala Cys Arg His Pro Asp His Leu Asp Cys | (SEQ ID NO: 69), |
| Ala Cys His Glu Thr His His Pro Asp Cys | (SEQ ID NO: 70), and | a fragment of said amino acid sequence or a variant of said amino acid sequence or fragment.

In other embodiments, the peptide mimotope of the present invention comprises an amino acid sequence selected from the group consisting of:

| | |
|---|---|
| Ser Phe Arg Asp Met Asn Tyr Ser Asp Tyr Phe Met | (SEQ ID NO: 71), |
| His Ile Leu Pro Leu Tyr Pro | (SEQ ID NO: 72), |
| Ser Pro Tyr Met Pro Met Gln | (SEQ ID NO: 73), |
| Asp Arg Cys Trp Leu Glu Gln Trp Pro Cys Arg Arg Asp Ser Asp Ile Pro | (SEQ ID NO: 74), |
| Gln Thr Cys Asp His Asp Thr Arg His Pro Thr Gly Asp Asp Leu Cys Arg Arg Asp Ser Asp Cys Gly Gly Asn Cys Ile Cys Arg Gly Asn Gly Tyr Cys Gly | (SEQ ID NO: 75), and | a fragment of said amino acid sequence or a variant of said amino acid sequence or fragment.

In one embodiment, the peptide mimotope is conjugated to at least one fusion partner. In one embodiment, the peptide mimotope is part of a fusion polypeptide. In one embodiment, the fusion partner comprises a heterologous amino acid sequence. In one embodiment, the fusion partner comprises a reporter for an immunological assay. In one embodiment, the reporter is selected from the group consisting of alkaline phosphatase, horseradish peroxidase, or a fluorescent molecule. In one embodiment, the fusion partner comprises a label.

In one embodiment, the peptide mimotope is stabilized by a covalent modification. Preferably, the modification is a cyclization. In one embodiment, cyclization is via a disulfide, a lactam, preferably a gamma-lactam, or another bridge.

In one embodiment, the peptide mimotopes and amino acid sequences of peptide mimotopes described herein are comprised by a structure conferring rigidity to the peptide mimotope or amino acid sequence. For example, the peptide mimotope or amino acid sequence may be inserted into a polypeptide or protein and may form a loop of said polypeptide or protein. In one particularly preferred embodiment, the peptide mimotopes described herein are cyclic peptides and the amino acid sequences of peptide mimotopes described herein are comprised by cyclic peptides.

In one embodiment, the peptide mimotope is present in oligomeric or multimeric form. In this embodiment, two or more peptide mimotopes of the invention which may be identical or different may be linked or coupled by covalent or non-covalent bonding, such as through biotin/streptavidin. Thus, peptide mimotopes of the invention may form dimers, trimers, tetramers etc.

The present invention further provides a recombinant nucleic acid which encodes a peptide mimotope of the invention. In one embodiment, the recombinant nucleic acid is in the form of a vector or in the form of RNA.

The present invention further provides a host cell comprising a recombinant nucleic acid of the invention.

The present invention further provides a method for assaying for the presence and/or amount of CLDN18.2 in a sample comprising using the peptide mimotope of the invention. In one embodiment, the peptide mimotope is used as a competitor of the CLDN18.2, e.g. for binding to an antibody against CLDN18.2

In particular, the present invention provides a method for determining whether a sample contains CLDN18.2 which comprises providing a monoclonal antibody against the CLDN18.2, reacting the monoclonal antibody with the sample in a reaction mixture containing the peptide mimotope of the invention as a competitor, and determining whether the sample contains CLDN18.2.

The present invention also provides a method for determining whether a sample contains CLDN18.2 which comprises: (a) incubating in a reaction the sample, a monoclonal antibody against the CLDN18.2, and a peptide mimotope of the invention which is a competitor of the CLDN18.2 for the monoclonal antibody; (b) detecting in the reaction a complex consisting of the CLDN18.2 bound by the monoclonal antibody and a complex formed by the mimotope and monoclonal antibody; and (c) comparing an amount of each of the complexes wherein a decrease in the amount of the complex comprising the peptide mimotope indicates that the sample contains CLDN18.2.

In one embodiment of the methods of the invention, the peptide mimotope is conjugated to a label or a reporter.

The present invention further provides a method for assaying for the presence and/or amount of binding agents to CLDN18.2 such as CLDN18.2 antibodies in a sample comprising using the peptide mimotope of the invention. Preferably, the peptide mimotope is used for capturing binding agents to CLDN18.2 such as CLDN18.2 antibodies in a sample.

The present invention further provides a method for capturing binding agents to CLDN18.2 such as CLDN18.2 antibodies in a sample comprising using the peptide mimotope of the invention.

In one embodiment, the methods of the invention are performed in the context of an immunoassay.

In particular, the present invention provides a method of determining CLDN18.2 antibodies in a sample which comprises contacting a sample with at least one peptide mimotope of the invention and assaying for the presence or absence of mimotope-antibody complexes, wherein the presence of the mimotope-antibody complexes is indicative of the presence of CLDN18.2 antibodies in the sample.

In one embodiment of the methods of the invention, the peptide mimotope is releasably or non-releasably immobilised on a solid support.

The present invention also provides a method of separating and/or purifying CLDN18.2 binding agents using the peptide mimotope of the invention. In this embodiment, the peptide mimotope can be used in the context of affinity chromatography. In particular, the method may comprise contacting a sample with at least one peptide mimotope of the invention and separating mimotope-CLDN18.2 binding agent complexes from other components of the sample. In one embodiment, the present invention provides a method of purifying a CLDN18.2 binding agent, comprising treating a sample comprising the CLDN18.2 binding agent with an immobilized peptide mimotope of the invention, a washing step to separate off unwanted compounds such as impurities, and an elution step to obtain the CLDN18.2 binding agent.

The present invention further provides a test reagent or kit comprising a peptide mimotope of the invention. In one embodiment, the test reagent or kit is a diagnostic reagent or kit. In one embodiment, the peptide mimotope is conjugated to a label. According to the invention, a label may be selected from the group consisting of a radioactive compound, a chemiluminescent compound, an electroactive compound, a fluorescent compound, and a direct particulate compound.

The test kit of the invention may further comprise at least one additional reagent for performing an immunoassay and/or instructions for use of the kit for performing an immunoassay.

The present invention further provides an assay device comprising a peptide mimotope of the invention. In one embodiment, the assay device is an enzyme-linked immunosorbent assay device. In one embodiment, the peptide mimotope is releasably or non-releasably immobilised on a solid support.

The present invention further provides a method for treating a subject exposed to a CLDN18.2 binding agent, e.g. with the aim of treating cancer, in particular cancer involving cells expressing CLDN18.2, comprising treating the organism with a peptide mimotope of the invention. In one embodiment, the peptide mimotope is antagonistic to the CLDN18.2 binding agent. In one embodiment, the peptide mimotope neutralizes binding of the CLDN18.2 binding agent to CLDN18.2.

The present invention further provides the peptide mimotope of the invention, the recombinant nucleic acid of the invention or the host cell of the invention for use in therapy, in particular for use in treating or preventing cancer in a patient, in particular cancer involving cells expressing CLDN18.2.

The present invention further provides a pharmaceutical composition comprising the peptide mimotope of the invention, the recombinant nucleic acid of the invention or the host cell of the invention.

The present invention further provides a method of treating a patient, e.g. a patient having cancer, in particular cancer involving cells expressing CLDN18.2, said patient preferably being exposed to a CLDN18.2 binding agent, comprising administering to the patient the pharmaceutical composition of the invention.

The present invention further provides a vaccine composition comprising a peptide mimotope of the invention.

The present invention further provides a method for eliciting antibodies against CLDN18.2 in a subject comprising treating the subject with a peptide mimotope of the invention.

In one embodiment of all aspects of the invention, CLDN18.2 is expressed in a cancer cell, preferably on the surface of a cancer cell.

According to the invention cancer cells expressing CLDN18.2 are preferably cancer cells of a cancer selected from the group consisting of gastric cancer, esophageal cancer, pancreatic cancer, lung cancer such as non small cell lung cancer (NSCLC), breast cancer, ovarian cancer, colon cancer, hepatic cancer, head-neck cancer, cancer of the gallbladder and the metastasis thereof, a Krukenberg tumor, peritoneal metastasis and/or lymph node metastasis.

In one embodiment of all aspects of the invention, cancer is preferably selected from the group consisting of gastric cancer, esophageal cancer, pancreatic cancer, lung cancer such as non small cell lung cancer (NSCLC), breast cancer, ovarian cancer, colon cancer, hepatic cancer, head-neck cancer, cancer of the gallbladder and the metastasis thereof, a Krukenberg tumor, peritoneal metastasis and/or lymph node metastasis.

In one embodiment of all aspects of the invention, CLDN18.2 preferably has the amino acid sequence according to SEQ ID NO: 1.

Other features and advantages of the instant invention will be apparent from the following detailed description and claims.

BRIEF DESCRIPTION OF THE DRAWINGS

FIG. 1A depicts phage ELISA binding analysis of 20 randomly picked clones from the 3rd screening round. Rituximab, hulgG Fc fragment and the secondary antibody ("2nd ab") were used to assess the specificity of the phage presented peptides. HuIgG Fc: Fc fragment of human IgG (Merck Millipore). 2nd ab: HRP conjugated goat anti-human IgG antibody (Sigma). The mean of two experiments is shown. SD values are presented as error bars. FIG. 1B depicts sequence alignment of selected clones having a common 'YPG' motif. The sequence alignment of all IMAB362 binding clones is represented as WebLogo (http://weblogo.berkeley.edu/).

FIG. 3A depicts comparison of the parental mimotope peptide 2a with the corresponding maturated variants 2b and 2c in the absence of serum. Control ab: antibody with identical chimerized backbone compared to IMAB362, directed against a different Claudin molecule. FIG. 3B depicts binding analysis of 2c to IMAB362 in the presence of 0-20% mouse serum. FIG. 3C depicts binding analysis of 2c to IMAB362 in the presence of 0-20% human serum. Data were fitted with Sigma Plot using a two-site saturation model.

FIG. 6A depicts a bispecific single chain antibody specific for CD3E on T-cells and CLDN18.2 on cancer target cells was pre-incubated with 20 µg/ml CLDN18.2 mimotope complexed with Neutravidin in a molar ratio of 1:8. Afterwards, the complex was incubated with NugC4 target cells. In parallel, untreated BiMAB was incubated with the cells as control. BiMAB binding to the respective cells was detected by staining with an anti-His antibody and an allophycocyanin-conjugated secondary antibody followed by FACS analysis. Each sample was run in duplicates and SD is shown by error bars.

FIG. 6B depicts NugC4 target cell lysis mediated by a bispecific single chain antibody specific for CD3ε on T-cells and CLDN18.2 on cancer target cells was assessed in a cytotoxicity assay. Different concentrations of the BiMAB were pre-incubated with 20 µg/ml of the CLDN18.2 mimotope complexed with Neutravidin in a molar ratio of 1:8 before incubation in presence of primary human T-cells and Luciferase-transfected NugC4 target cells for 24 hrs. Afterwards, luciferin was added to the cells and luminescence was measured in a plate reader. To calculate the specific lysis, minimum (NugC4 cells and T-cells) and maximum (NugC4 cells and T-cells after addition of Triton-X-100 in a final concentration of 2%) lysis was used. As a control the same assay was performed without the addition of the mimotope complex. The data shows mean values of triplicates with the corresponding SD shown by error bars.

DETAILED DESCRIPTION OF THE INVENTION

Figure 1B:
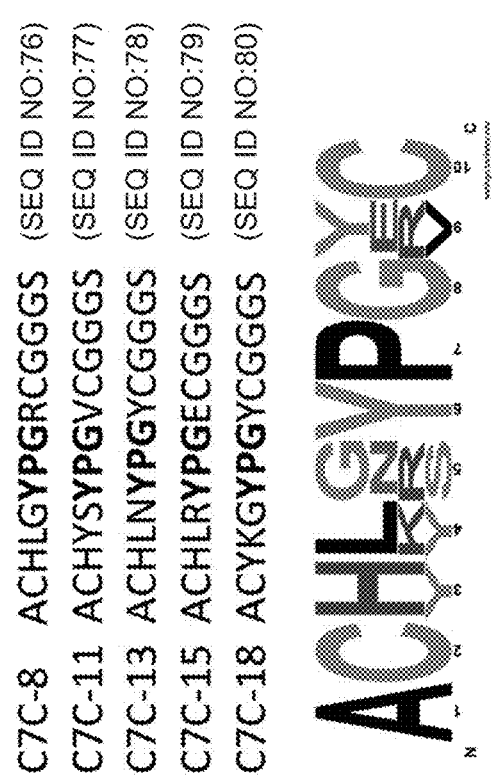
FIG. 1A and FIG. 1B. Single phage clone analysis.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölb, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2nd Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subjectmatter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop, termed EC1 or ECL1, consists on average of 53 amino acids, and the second extracellular loop, termed EC2 or ECL2, consists of around 24 amino acids. Cell surface proteins of the claudin family, such as CLDN18.2, are expressed in tumors of various origins, and are particularly suited as target structures in connection with antibody-mediated cancer immunotherapy due to their selective expression (no expression in a toxicity relevant normal tissue) and localization to the plasma membrane.

The term "CLDN" as used herein means claudin and includes CLDN18.2. Preferably, a claudin is a human claudin.

The term "CLDN18" relates to claudin 18 and includes any variants, including claudin 18 splice variant 1 (claudin 18.1 (CLDN18.1)) and claudin 18 splice variant 2 (claudin 18.2 (CLDN18.2)).

The term "CLDN18.2" preferably relates to human CLDN18.2, and, in particular, to a protein comprising, preferably consisting of the amino acid sequence according to SEQ ID NO: 1 of the sequence listing or a variant of said amino acid sequence. The first extracellular loop of CLDN18.2 preferably comprises amino acids 27 to 81, more preferably amino acids 29 to 78 of the amino acid sequence shown in SEQ ID NO: 1. The second extracellular loop of CLDN18.2 preferably comprises amino acids 140 to 180 of the amino acid sequence shown in SEQ ID NO: 1. Said first and second extracellular loops preferably form the extracellular portion of CLDN18.2.

CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

According to the invention, the term "claudin positive cancer" or similar terms means a cancer involving cancer cells expressing a claudin, preferably on the surface of said cancer cells.

"Cell surface" is used in accordance with its normal meaning in the art, and thus includes the outside of the cell which is accessible to binding by proteins and other molecules A claudin is expressed on the surface of cells if it is located at the surface of said cells and is accessible to binding by claudin-specific antibodies added to the cells.

The term "extracellular portion" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

The terms "part" or "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope or peptide is preferably immunologically equivalent to the epitope or peptide it is derived from. A part or fragment of a protein sequence preferably comprises a sequence of at least 6, in particular at least 8, at least 12, at least 15, at least 20, at least 30, at least 50, or at least 100 consecutive amino acids of the protein sequence.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1.5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cells.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cells. Preferably, CLDN18.2 expressed in a cell is expressed or exposed on the surface of said cell.

According to the present invention the term "mimotope" refers to a molecule which is a mimic of an epitope. The mimotope may also act as a competitor for the epitope of which it is a mimic in in vitro assays (e.g. ELISA assays) and preferably binds to the same antigen-binding region of an antibody which binds immunospecifically to an epitope of a desired antigen. The mimotope may elicit an immunological response in a host that is reactive to the antigen of which it is a mimic.

According to the invention, peptide mimotopes can be synthetically produced by chemical synthesis methods which are well known in the art, either as an isolated peptide or as a part of another peptide or polypeptide. Alternatively, a peptide mimotope can be produced in a microorganism which produces the peptide mimotope which is then isolated and if desired, further purified. Thus, the peptide mimotope can be produced in microorganisms such as bacteria, yeast, or fungi; in a eukaryote cells such as mammalian or insect cells; or, in a recombinant virus vector such as adenovirus, poxvirus, herpesvirus, Simliki forest virus, baculovirus, bacteriophage, sindbis virus, or sendai virus. Suitable bacteria for producing the peptide mimotope include *Escherichia coli, Bacillus subtilis*, or any other bacterium that is capable of expressing peptides such as the peptide mimotope. Suitable yeast types for expressing the peptide mimotope include, but are not limited to *Saccharomyces cerevisiae, Schizosaccharomyces pombe, Candida*, or any other yeast capable of expressing peptides. Methods for using the aforementioned bacteria, recombinant virus vectors, eukaryote cells to produce peptides are well known in the art.

To produce the peptide mimotope, the nucleic acid encoding the peptide mimotope is preferably in a plasmid and the nucleic acid is operably linked to a promoter which effects expression of the peptide mimotope in a microorganism. Suitable promoters include, but are not limited to, T7 phage promoter, T3 phage promoter, β-galactosidase promoter, and the Sp6 phage promoter. Methods for isolating and purifying peptides are well known in the art and include methods such as gel filtration, affinity chromatography, ion exchange chromatography, or centrifugation.

The peptide mimotopes, either by themselves or as part of a fusion peptide, can be conjugated to a heterologous peptide or protein. Such heterologous proteins include, but are not limited to, carrier proteins such as bovine serum albumen (BSA), and reporter enzymes which include, but are not limited to, horseradish peroxidase or alkaline phosphatase. Further, the peptide mimotopes or fusion peptides comprising the peptide mimotope can be chemically conjugated to fluorescent reporter molecules which include, but are not limited to, fluorescein or R-phycoerythrin. Methods for conjugating carrier proteins, enzymes, and fluorescent reporter molecules to peptides and fusion peptides are well known in the art.

To facilitate isolation of the peptide mimotope, a fusion polypeptide can be made wherein the peptide mimotope is translationally fused (covalently linked) to a heterologous tag such as a heterologous polypeptide or polyhistidine, preferably six histidine residues, which allows for the simplified recovery of the fusion polypeptide, e.g. its isolation by affinity chromatography or metal affinity chromatography, preferably nickel affinity chromatography. In some instances it can be desirable to remove the tag after purification. Therefore, it is also contemplated that the fusion polypeptide comprises a cleavage site at the junction between the peptide mimotope and the heterologous tag. The cleavage site consists of an amino acid sequence that is cleaved with an enzyme specific for the amino acid sequence at the site.

The peptide mimotopes described herein can be used as a control or competitor in immunoassays for detecting CLDN18.2 and can be used for detecting CLDN18.2 binding molecules such as CLDN18.2 antibodies. The peptide mimotopes can further be used in therapies for treating animals or humans exposed to CLDN18.2 binding molecules such as therapeutic CLDN18.2 antibodies, e.g. for modulating, in particular reducing, the activity of the CLDN18.2 binding molecule.

For example, the peptide mimotopes, either alone, or as a component of a fusion polypeptide, such as conjugated to a carrier protein or fluorescent reporter molecule, are useful as standard and conjugates in immunoassays such as ELISAs and RIAS, which are used to determine whether a sample contains CLDN18.2. In such immunoassays, the use of CLDN18.2 as a control or as a competitor has been difficult. Therefore, the peptide mimotopes provide a significant advantage over CLDN18.2.

In general, the immunoassays are performed using an enzyme-linked immunosorbent assay (ELISA) embodiment.

A microtiter plate may be provided containing a plurality of wells wherein a first well or series of wells contains a monoclonal antibody against CLDN18.2 immobilized to the surface therein. A sample may be mixed with the peptide mimotope and the mixture added to the wells containing the bound monoclonal antibody. The mimotope peptide may be part of a fusion polypeptide. The CLDN18.2 in the sample and the peptide mimotope compete for binding to the monoclonal antibody. The ELISA is incubated for a time sufficient for antibody complexes to form. Afterwards, the wells are washed to remove any unbound material. The wells may then be incubated with a labeled antibody or an antibody conjugated to a reporter molecule that binds to the fusion polypeptide to form a complex which can be detected. A detectable signal from the reporter may indicate that the sample does not contain CLDN18.2 whereas an absence of a signal may indicate that the sample contains CLDN18.2 which had bound all of the monoclonal antibody, thereby preventing the peptide mimotope from binding the monoclonal antibody immobilized in the wells. When the fusion polypeptide comprises a label or reporter molecule such as a reporter enzyme such as alkaline phosphatase, the antibody-mimotope peptide complex can be detected directly without the need for a labeled antibody.

Alternatively, a microtiter plate may be provided containing a plurality of wells wherein a first well or series of wells contains the peptide mimotope, which may be conjugated to a carrier protein or fusion polypeptide, immobilized to the surface therein. Sample may be added to the wells containing the bound peptide mimotopes along with a constant amount of a monoclonal antibody against CLDN18.2. The CLDN18.2 in the sample and the peptide mimotope bound to the well surfaces compete for binding to the monoclonal antibody. The ELISA is incubated for a time sufficient for antibody complexes to form. Afterwards, the wells are washed to remove any unbound material. The amount of monoclonal antibody that is bound to the immobilized mimotope peptides in the well is determined by incubating the wells with a labeled antibody or an antibody conjugated to a reporter molecule that binds to the antibody against CLDN18.2 to form a complex that can be detected. A detectable signal from the reporter indicates the sample does not contain CLDN18.2 whereas an absence of a signal indicates that the sample contains CLDN18.2 which had bound all of the antibody against CLDN18.2, thereby preventing the antibody from binding the peptide mimotope immobilized in the wells. The intensity of the signal provides an estimate of the relative concentration of CLDN18.2 in the sample. Alternatively, the antibody against CLDN18.2 can be labeled with a reporter in which case the bound antibody can be detected directly without the need for a labeled antibody. In either case, detection is by methods well known in the art for detecting the particular reporter ligand.

Instead of an ELISA, the peptide mimotopes can be used in a radio immunoassay (RIA) for detecting CLDN18.2 in a sample. The RIA procedure may involve incubation of a monoclonal antibody against CLDN18.2, simultaneously with a solution of unknown sample or known standard, and a constant amount of radioactively labeled peptide mimotope or fusion polypeptide. After separation of the free peptide mimotope or fusion polypeptide from bound peptide mimotope or fusion polypeptide, the radioactivity in the respective fractions is determined. The concentration of CLDN18.2 in the unknown sample is determined by comparing results to a standard curve. Several known methods may be used for the separation of free from bound peptide mimotope or fusion polypeptide in the RIA. Radioactivity may be determined in a liquid scintillation counter.

According to the invention, the CLDN18.2 which is to be assayed may be expressed on the surface of a cell.

Mimotopes of the invention may also be used in methods for detecting the presence of antibodies against CLDN18.2. The design of suitable immunoassays to put these methods into effect may be subject to a great deal of variation, and a variety of these immunoassays are known in the art. Suitable immunoassay protocols may be based, for example, upon competition, or direct reaction, or sandwich type assays. The immunoassay protocols used may also, for example, use solid supports, or may be by immunoprecipitation. Assays may involve the use of labelled antibodies and the labels may be, for example, fluorescent, chemiluminescent, radioactive, or dye molecules. Particular preferred assays are enzyme-labelled and mediated immunoassays, such as ELISA assays.

Accordingly, the peptide mimotopes may also be used in an assay such as an ELISA assay to determine antibody against CLDN18.2 in a sample. For this purpose, the wells of ELISA plates may be coated with peptide mimotopes. Subsequently, a sample such as plasma may be added and the detection of peptide specific antibodies (primary antibody) may be performed with a labelled secondary antibody directed against the primary antibody.

Mimotopes of the invention may be bound to a solid support, for example the surface of an immunoassay well or dipstick, and/or packaged into kits in a suitable container along with suitable reagents, controls, instructions and the like.

Accordingly the present invention also provides a kit comprising at least one mimotope of the present invention. In a preferred embodiment, the kit further comprises at least one additional agent such as one or more suitable reagents for performing an immunoassay, a control, or instructions for use of the kit.

When used as an assay reagent as described herein, a mimotope of the invention may be conjugated to a label. Preferably, the label is any entity the presence of which can be readily detected. Preferably the label is a direct label. Direct labels are entities which, in their natural state, are readily visible either to the naked eye, or with the aid of an optical filter and/or applied stimulation, e.g. UV light to promote fluorescence. Examples include radioactive, chemiluminescent, electroactive (such as redox labels), and fluorescent compounds. Direct particulate labels, such as dye sols, metallic sols (e.g. gold) and coloured latex particles, are also very suitable and are, along with fluorescent compounds, preferred. Of these options, coloured latex particles and fluorescent compounds are most preferred. Concentration of the label into a small zone or volume should give rise to a readily detectable signal, e.g. a strongly coloured area. Indirect labels, such as enzymes, e.g. alkaline phosphatase and horseradish peroxidase, can also be used, although these usually require the addition of one or more developing reagents such as substrates before a visible signal can be detected.

Conjugation of the label to the mimotope of the invention can be by covalent or non-covalent (including hydrophobic) bonding, or by adsorption. Techniques for such conjugation are commonplace in the art and may be readily adapted for the particular reagents employed.

According to the invention there is further provided an assay device comprising at least one mimotope of the present invention. In one embodiment, the assay device is selected from the group consisting of an enzyme-linked immunosorbent assay device.

Such a device can take different forms, and it can be varied depending on the precise nature of the assay being performed. For example, the mimotope of the invention may be coated onto a solid support, typically nitrocellulose or other hydrophobic porous material. Alternatively, the mimotope may be coated on a synthetic plastics material, microtitre assay plate, microarray chip, latex bead, filter comprising a cellulosic or synthetic polymeric material, glass or plastic slide, dipstick, capillary fill device and the like. Coating of the mimotopes to these surfaces can be accomplished by methods known in the art. Protein carriers are typically used for complexing, with BSA or adhesive peptides being the most preferred. In one embodiment, the mimotope of the invention is releasably immobilised on the solid support. In a further preferred embodiment, the diagnostic reagent is nonreleasably immobilised on the solid support.

The mimotopes of the invention may be further used as vaccines so as to induce CLDN18.2 antibodies or for modulating the activity of CLDN18.2 binding agents such as CLDN18.2 antibodies, in particular bispecific antibodies binding to CLDN18.2. To this end, the mimotopes of the invention may be combined with various components to produce pharmaceutically acceptable compositions.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes cancer, in particular those forms of cancer described herein. Any reference herein to cancer or particular forms of cancer also includes cancer metastasis thereof. In a preferred embodiment, a disease to be treated according to the present application involves cells expressing CLDN18.2.

"Diseases involving cells expressing CLDN18.2" or similar expressions means according to the invention that CLDN18.2 is expressed in cells of a diseased tissue or organ. In one embodiment, expression of CLDN18.2 in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving cells expressing CLDN18.2 include cancer diseases. Furthermore, according to the invention, cancer diseases preferably are those wherein the cancer cells express CLDN18.2.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing CLDN18.2 and a cancer cell expresses CLDN18.2. A cell expressing CLDN18.2 preferably is a cancer cell, preferably of the cancers described herein.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential.

In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy of the invention is metastasis originating from gastric cancer as primary site. In preferred embodiments such gastric cancer metastasis is Krukenberg tumors, peritoneal metastasis and/or lymph node metastasis.

Krukenberg tumor is an uncommon metastatic tumor of the ovary accounting for 1% to 2% of all ovarian tumors. Prognosis of Krukenberg tumor is still very poor and there is no established treatment for Krukenberg tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "immunization" or "vaccination" describe the process of administering an antigen to an individual with the purpose of inducing an immune response, for example, for therapeutic or prophylactic reasons.

The terms "protect", "prevent", "prophylactic", "preventive", or "protective" relate to the prevention and/or treatment of the occurrence and/or the propagation of a disease, e.g. tumor, in an individual. For example, a prophylactic administration of a therapy can protect the receiving individual from the development of a disease.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

"Target cell" shall mean any undesirable cell such as a cancer cell. In preferred embodiments, the target cell expresses CLDN18.2.

The term "antigen" relates to an agent comprising an epitope against which an immune response is to be generated and/or is directed. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen or a processing product thereof is preferably recognizable by a T or B cell receptor, or by an immunoglobulin molecule such as an antibody. In a preferred embodiment, the antigen is a disease-associated antigen, such as a tumor antigen, a viral antigen, or a bacterial antigen.

In the context of the present invention, the term "tumor antigen" or "tumor-associated antigen" preferably relates to proteins that are under normal conditions specifically expressed in a limited number of tissues and/or organs or in specific developmental stages and are expressed or aberrantly expressed in one or more tumor or cancer tissues. In the context of the present invention, the tumor-associated antigen is preferably associated with the cell surface of a cancer cell and is preferably not or only rarely expressed in normal tissues. For example, CLDN18.2 has been identified as differentially expressed in tumor tissues, with the only normal tissues expressing CLDN18.2 being stomach The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

According to the invention, the term "binding agent to CLDN18.2" includes any compound that has a binding capacity to CLDN18.2. Preferably, such binding agent comprises at least one binding domain for CLDN18.2. The term includes molecules such as antibodies and antibody fragments, bispecific or multispecific molecules and chimeric antigen receptors (CARs). The term also includes all artificial binding molecules (scaffolds) having a binding capacity to CLDN18.2 including but not limited to nanobodies, affibodies, anticalins, DARPins, monobodies, avimers, and microbodies. In one embodiment said binding agent binds to an extracellular domain of CLDN18.2. In one embodiment said binding agent binds to native epitopes of CLDN18.2 present on the surface of living cells. In one embodiment said binding agent binds to the first extracellular loop of CLDN. In one embodiment said binding to CLDN18.2 is a specific binding.

In one embodiment the binding domain binding to CLDN18.2 comprises a variable domain of a heavy chain of an immunoglobulin (VH) with a specificity for a claudin 18.2 antigen (VH(CLDN18.2)) and a variable domain of a light chain of an immunoglobulin (VL) with a specificity for a claudin 18.2 antigen (VL(CLDN18.2)).

In one embodiment said VH(CLDN18.2) comprises an amino acid sequence represented by SEQ ID NO: 2 or a fragment thereof or a variant of said amino acid sequence or fragment and the VL(CLDN18.2) comprises an amino acid sequence represented by SEQ ID NO: 3 or a fragment thereof or a variant of said amino acid sequence or fragment.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely.

Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ)) or an IgG4 antibody (e.g. IgG4, κ, λ).

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The antibodies described herein are preferably isolated. An "isolated antibody" as used herein, is intended to refer to an antibody which is substantially free of other antibodies having different antigenic specificities (e.g., an isolated antibody that specifically binds to CLDN18.2 is substantially free of antibodies that specifically bind antigens other than CLDN18.2). An isolated antibody that specifically binds to an epitope, isoform or variant of human CLDN18.2 may, however, have cross-reactivity to other related antigens, e.g., from other species (e.g., CLDN18.2 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition or mixture.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "binding domain" characterizes in connection with the present invention a structure, e.g. of an antibody, which binds to/interacts with a given target structure/antigen/epitope. Thus, the binding domain according to the invention designates an "antigen-interaction-site".

All antibodies and derivatives of antibodies such as antibody fragments as described herein for the purposes of the invention are encompassed by the term "antibody". The term "antibody derivatives" refers to any modified form of an antibody, e.g., a conjugate of the antibody and another agent or antibody, or an antibody fragment. Furthermore, the antibodies and derivatives of antibodies as described herein are useful for producing binding agents of the invention such as antibody fragments.

Naturally occurring antibodies are generally monospecific, i.e. they bind to a single antigen. The present invention also envisions binding agents which are bispecific or multispecific molecules binding to CLDN18.2 and to one or more further antigens. Particularly preferred are binding agents binding to a cytotoxic cell (e.g. by engaging the CD3 receptor) and a cancer cell (by engaging CLDN18.2). Such binding agents are at least bispecific or multispecific such as trispecific, tetraspecific and so on.

Thus, in one embodiment, a binding agent according to the invention comprises at least two binding domains, wherein a first binding domain binds to CLDN18.2 and a second binding domain binds to CD3. Such binding agent may bind to a cytotoxic cell (e.g. by engaging the CD3 receptor) and a cancer cell expressing CLDN18.2 to be destroyed as a target.

The bispecific or multispecific binding agent may be in the format of an antibody molecule or of an antibody-like molecule or of a protein scaffold with antibody-like properties or of a cyclic peptide with at least two binding specificities. Thus, the binding agent may comprise one or more antibodies as described herein or fragments thereof.

According to the invention, a bispecific molecule, in particular a bispecific protein, such as a bispecific antibody is a molecule that has two different binding specificities and thus may bind to two different types of antigen such as CLDN18.2 and CD3. Particularly, the term "bispecific antibody" as used herein refers to an antibody comprising two antigen-binding sites, a first binding site having affinity for a first antigen or epitope and a second binding site having binding affinity for a second antigen or epitope distinct from the first. In particular, a bispecific antibody is an artificial protein that is composed of fragments of two different antibodies (said fragments of two different antibodies forming two binding domains) and consequently binds to two different types of antigen. A bispecific antibody preferably is engineered to simultaneously bind to an immune cell, such as an immune effector cell, in particular a T cell such as a cytotoxic cell (e.g. by binding to CD3) and a target cell like a cancer cell (by binding to the tumor-associated antigen CLDN18.2) to be destroyed.

The term "bispecific antibody" also includes diabodies. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

"Multispecific binding agents" are molecules which have more than two different binding specificities.

Particularly preferred according to the invention are bispecific antibodies including bispecific antibody fragments, in particular bispecific single chain antibodies including bispecific single chain antibody fragments. The term "bispecific single chain antibody" denotes a single polypeptide chain comprising two binding domains. In particular, the term "bispecific single chain antibody" or "single chain bispecific antibody" or related terms in accordance with the present invention preferably mean antibody constructs resulting from joining at least two antibody variable regions in a single polypeptide chain devoid of the constant and/or Fc portion(s) present in full immunoglobulins.

For example, a bispecific single chain antibody may be a construct with a total of two antibody variable regions, for example two VH regions, each capable of specifically binding to a separate antigen, and connected with one another through a short polypeptide spacer such that the two antibody variable regions with their interposed spacer exist as a single contiguous polypeptide chain. Another example of a bispecific single chain antibody may be a single polypeptide chain with three antibody variable regions. Here, two antibody variable regions, for example one VH and one VL, may make up an scFv, wherein the two antibody variable regions are connected to one another via a synthetic polypeptide linker, the latter often being genetically engineered so as to be minimally immunogenic while remaining maximally resistant to proteolysis. This scFv is capable of specifically binding to a particular antigen, and is connected to a further antibody variable region, for example a VH region, capable of binding to a different antigen than that bound by the scFv. Yet another example of a bispecific single chain antibody may be a single polypeptide chain with four antibody variable regions. Here, the first two antibody variable regions, for example a VH region and a VL region, may form one scFv capable of binding to one antigen, whereas the second VH region and VL region may form a second scFv capable of binding to another antigen. Within a single contiguous polypeptide chain, individual antibody variable regions of one specificity may advantageously be separated by a synthetic polypeptide linker, whereas the respective scFvs may advantageously be separated by a short polypeptide spacer as described above.

According to one embodiment of the invention, the first binding domain of the bispecific antibody comprises one antibody variable domain, preferably a VHH domain. According to one embodiment of the invention, the first binding domain of the bispecific antibody comprises two antibody variable domains, preferably a scFv, i.e. VH-VL or VL-VH. According to one embodiment of the invention, the second binding domain of the bispecific antibody comprises one antibody variable domain, preferably a VHH domain. According to one embodiment of the invention, the second binding domain of the bispecific antibody comprises two antibody variable domains, preferably a scFv, i.e. VH-VL or VL-VH. In its minimal form, the total number of antibody variable regions in the bispecific antibody according to the invention is thus only two. For example, such an antibody could comprise two VH or two VHH domains.

According to one embodiment of the invention, the first binding domain and the second binding domain of the bispecific antibody each comprise one antibody variable domain, preferably a VHH domain. According to one embodiment of the invention, the first binding domain and the second binding domain of the bispecific antibody each comprise two antibody variable domains, preferably a scFv, i.e. VH-VL or VL-VH. In this embodiment, the binding agent of the invention preferably comprises (i) a heavy chain variable domain (VH) of a CLDN18.2 antibody, (ii) a light chain variable domain (VL) of a CLDN18.2 antibody, (iii) a heavy chain variable domain (VH) of an antibody to a second antigen, e.g. of a CD3 antibody and (iv) a light chain variable domain (VL) of an antibody to a second antigen, e.g. of a CD3 antibody.

Bispecific full-length antibodies may be obtained by covalently linking two monoclonal antibodies or by conventional hybrid-hybridoma techniques. Covalent linking of two monoclonal antibodies is described in Anderson, Blood 80 (1992), 2826-34. In the context of this invention, one of the antibodies may be specific for CLDN18.2 and the other one for CD3.

In one embodiment, the bispecific binding agent is in the format of an antibody-like molecule with a heavy chain containing two consecutive N-terminal variable domains with different specificities and a light chain with two consecutive variable domains with different specificities resulting in four binding domains with two different specificities (Wu et al., Nat. Biotechnology, 2007, 25(11)), wherein one specificity may be CD3 and the other specificity is CLDN18.2.

In a preferred embodiment, the bispecific binding agent of the invention is in the format of an antibody fragment.

In one embodiment, the bispecific molecules according to the invention comprises two Fab regions, e.g. one being directed against CLDN18.2 and the other being directed against CD3. In one embodiment, the molecule of the invention is an antigen binding fragment (Fab)2 complex. The Fab2 complex is composed of two Fab fragments, one Fab fragment comprising a Fv domain, i.e. VH and VL domains, e.g. specific for a CD3 antigen, and the other Fab fragment comprising a Fv domain specific for CLDN18.2. Each of the Fab fragments may be composed of two single chains, a VL-CL module and a VH-CH module. Alternatively, each of the individual Fab fragments may be arranged in a single chain, preferably, VL-CL-CH-VH, and the individual variable and constant domains may be connected with a peptide linker. In general, the individual single chains and Fab fragments may be connected via disulfide bonds, adhesive domains, chemically linked and/or peptide linker. The bispecific molecule may also comprise more than two Fab fragments, in particular, the molecule may be a Fab3, Fab4, or a multimeric Fab complex with specificity for 2, 3, 4, or more different antigens. The invention also includes chemically linked Fabs.

In one embodiment, the binding agent according to the invention includes various types of bivalent and trivalent single-chain variable fragments (scFvs), fusion proteins mimicking the variable domains of two antibodies. A single-chain variable fragment (scFv) is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. Divalent (or bivalent) single-chain variable fragments (di-scFvs, bi-scFvs) can be engineered by linking two scFvs. This can be done by producing a single peptide chain with two VH and two VL regions, yielding tandem scFvs. The invention also includes multispecific molecules comprising more than two scFvs binding domains. This makes it possible that the molecule comprises either multiple antigen specificities and is a trispecific, tetraspecific, or multispecific molecule, or the molecule is a bispecific molecule comprising more than one scFv binding domain with specificity for the same antigen. In particular, the molecule of the invention may be a multispecific single chain Fv.

Another possibility is the creation of scFvs with linker peptides that are too short for the two variable regions to fold together (about five amino acids), forcing scFvs to dimerize. This type is known as diabodies. Still shorter linkers (one or two amino acids) lead to the formation of trimers, so-called triabodies or tribodies. Tetrabodies have also been produced. They exhibit an even higher affinity to their targets than diabodies.

A particularly preferred example of a bispecific antibody fragment is a diabody (Kipriyanov, Int. J. Cancer 77 (1998), 763-772), which is a small bivalent and bispecific antibody fragment. Diabodies comprise a heavy chain variable domain (VH) connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites. To construct bispecific diabodies, the V-domains of e.g. an anti-CD3 antibody and an anti-CLDN18.2 antibody may be fused to create the two chains VH(CD3)-VL(CLDN18.2), VH(CLDN18.2)-VL(CD3). Each chain by itself is not able to bind to the respective antigen, but recreates the functional antigen binding sites on pairing with the other chain. To this end, a peptide linker that is too short to allow pairing between the two domains on the same chain is used. The two scFv molecules, with a linker between heavy chain variable domain and light chain variable domain that is too short for intramolecular dimerization, are co-expressed and self assemble to form bi-specific molecules with the two binding sites at opposite ends.

In one embodiment, the multispecific molecule according to the invention comprises variable (VH, VL) and constant domains (C) of immunoglobulins. In one embodiment the bispecific molecule is a minibody, preferably, a minibody comprising two single VH-VL-C chains that are connected with each other via the constant domains (C) of each chain. According to this aspect, the corresponding variable heavy chain regions (VH), corresponding variable light chain regions (VL) and constant domains (C) may be arranged, from N-terminus to C-terminus, in the order VH(CLDN18.2)-VL(CLDN18.2)-(C) and VH(CD3)-VL(CD3)-C, wherein C is preferably a CH3 domain. Pairing of the constant domains results in formation of the minibody.

According to another particularly preferred aspect, the bispecific binding agent of the invention is in the format of a bispecific single chain antibody construct, whereby said construct comprises or consists of at least two binding domains, whereby one of said domains binds to CLDN18.2 and a second domain binds to another antigen, e.g. CD3. Such molecules, also termed "bispecific T cell engagers" (BiTEs; the term BiTE only refers to bi-specific molecules of which one arm is specific for CD3) consist of two scFv molecules connected via a linker peptide.

As used herein, a "bispecific single chain antibody" denotes a single polypeptide chain comprising two binding domains. Each binding domain comprises one variable region from an antibody heavy chain ("VH region"), wherein the VH region of the first binding domain specifically binds to the CLDN18.2, and the VH region of the second binding domain specifically binds to another antigen, e.g. CD3. The two binding domains are optionally linked to one another by a short polypeptide spacer. A non-limiting example for a polypeptide spacer is Gly-Gly-Gly-Gly-Ser (G-G-G-G-S) (SEQ ID NO: 7) and repeats thereof. Each binding domain may additionally comprise one variable region from an antibody light chain ("VL region"), the VH region and VL region within each of the first and second binding domains being linked to one another via a polypeptide linker long enough to allow the VH region and VL region of the first binding domain and the VH region and VL region of the second binding domain to pair with one another.

According to this aspect, the corresponding variable heavy chain regions (VH) and the corresponding variable light chain regions (VL) are arranged, from N-terminus to C-terminus, in the order VH(CLDN18.2)-VL(CLDN18.2)-VH(CD3)-VL(CD3), VH(CD3)-VL(CD3)-VH (CLDN18.2)-VL(CLDN18.2) or VH(CD3)-VL(CD3)-VL (CLDN18.2)-VH(CLDN18.2). It is, however, also envisaged that the bispecific single chain antibodies of the invention comprise other domain arrangements, such as VL(CLDN18.2)-VH(CLDN18.2)-VH(CD3)-VL(CD3), VL(CLDN18.2)-VH(CLDN18.2)-VL(CD3)-VH(CD3), VH(CLDN18.2)-VL(CLDN18.2)-VL(CD3)-VH(CD3), VL(CD3)-VH(CD3)-VH(CLDN18.2)-VL(CLDN18.2), VL(CD3)-VH(CD3)-VL(CLDN18.2)-VH(CLDN18.2). "CD3" is only given herein as an example to designate a second binding specificity to an antigen.

A long linker generally connects the corresponding variable heavy chain regions (VH) and the corresponding variable light chain regions (VL) to create a scFv binding domain while a short linker generally connects two scFv binding domains. The linker is generally designed to provide flexibility and protease resistance, and preferably, the linker comprises glycine and/or serine amino acid residues. Short peptide linkers may consist of 12 or less such as 11, 10, 9, 8, 7, 6, 5, 4, 3 or 2 amino acids, and preferably, 5 or 6 amino acids. Short peptide linkers preferably comprise the amino acid sequences SGGGGS (SEQ ID NO: 6) or GGGGS (SEQ ID NO: 7).

Long peptide linkers may consist of 12 or more, such as 15 to 25 or 15 to 20 or 15 to 18 amino acids. Long peptide linkers preferably comprise the amino acid sequences (GGGGS)3 (SEQ ID NO: 4) or VE(GGSGGS)2GGVD (SEQ ID NO: 8). Further long peptide linkers may comprise the amino acid sequences (GGGGS)4 (SEQ ID NO: 9), (GGGGS)5 (SEQ ID NO: 10) or GGGGS(GGS)3GGGS (SEQ ID NO: 11).

Binding agents according to the invention may also comprises an amino acid sequence for facilitating secretion of the molecule, such as a N-terminal secretion signal, and/or one or more epitope tags facilitating binding, purification or detection of the molecule.

Preferably, the secretion signal is a signal sequence that allows a sufficient passage through the secretory pathway and/or secretion of the binding agent into the extracellular environment. Preferably, the secretion signal sequence is cleavable and is removed from the mature binding agent. The secretion signal sequence preferably is chosen with respect to the cell or organism wherein the binding agent is produced in.

The amino acid sequence of an epitope tag may be introduced to any position within the amino acid sequence of the binding agent, and may take the shape of a loop within the encoded protein structure, or it may be N-terminally or C-terminally fused to the binding agent. Preferably, the epitope tag is C-terminally fused to the binding agent. The epitope tag may contain a cleavage site that allows a removal of the tag from the binding agent. Said epitope tag can be any kind of epitope tag that is functional under native and/or denaturing conditions, preferable a histidin tag, most preferable a tag comprising six histidins.

The bispecific binding agent of the invention may contain, in addition to said first and second binding domain, a further binding domain which serves e.g. to enhance selectivity for tumor cells. This can be achieved e.g. by providing binding domains that bind to other antigens expressed on tumor cells.

According to the invention, the term "binding agent to CLDN18.2" further includes chimeric antigen receptors (CAR). According to the invention the term "chimeric antigen receptor (CAR)" is synonymous with the terms "chimeric T cell receptor" and "artificial T cell receptor".

These terms relate to engineered receptors, which confer an arbitrary specificity such as the specificity of a monoclonal antibody onto an immune effector cell such as a T cell. In this way, a large number of cancer-specific T cells can be generated for adoptive cell transfer. Thus, an artificial T cell receptor may be present on T cells, e.g. instead of or in addition to the T cell's own T cell receptor. Such T cells do not necessarily require processing and presentation of an antigen for recognition of the target cell but rather may recognize preferably with specificity any antigen present on a target cell. Preferably, said artificial T cell receptor is expressed on the surface of the cells. For the purpose of the present invention T cells comprising an artificial T cell receptor are comprised by the term "T cell" as used herein.

In one embodiment, a single-chain variable fragment (scFv) derived from a monoclonal antibody is fused to CD3-zeta transmembrane and endodomain. Such molecules result in the transmission of a zeta signal in response to recognition by the scFv of its antigen target on a target cell and killing of the target cell that expresses the target antigen. Antigen recognition domains which also may be used include among others T-cell receptor (TCR) alpha and beta single chains. In fact almost anything that binds a given target with high affinity can be used as an antigen recognition domain.

Following antigen recognition, receptors cluster and a signal is transmitted to the cell. The most commonly used endodomain component is CD3-zeta. This transmits an activation signal to the T cell after antigen is bound.

Adoptive cell transfer therapy with CAR-engineered T cells expressing chimeric antigen receptors is a promising anti-cancer therapeutic as CAR-modified T cells can be engineered to target virtually any tumor antigen. For example, patient's T cells may be genetically engineered to express CARs specifically directed towards antigens on the patient's tumor cells, then infused back into the patient.

In the context of the present invention, the binding agents are preferably therapeutically effective and/or are capable of eliciting immune effector functions as described herein. Preferably, said immune effector functions are directed against cells carrying the tumor antigen CLDN18.2 on their surface such as cancer cells.

The term "therapeutically effective" relates to a therapeutic effectiveness when administered to an individual. The term "therapeutically effective" further relates to the ability to change, preferably cure, alleviate or partially arrest the clinical manifestations of a given disease and its complications in a therapeutic intervention.

The term "immune effector functions" in the context of the present invention includes any functions mediated by components of the immune system that result e.g. in the inhibition of tumor growth and/or inhibition of tumor development, including inhibition of tumor dissemination and metastasis. Preferably, immune effector functions result in killing of tumor cells. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor-associated antigen, cytolysis of the cells carrying the tumor-associated antigen, and/or inhibition of proliferation of the cells carrying the tumor-associated antigen. Binding agents may also exert an effect simply by binding to tumor-associated antigens on the surface of a cancer cell. For example, antibodies may block the function of the tumor-associated antigen or induce apoptosis just by binding to the tumor-associated antigen on the surface of a cancer cell.

ADCC describes the cell-killing ability of effector cells, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

The binding agents described herein may be conjugated to a therapeutic moiety or agent, such as a cytotoxin, a drug (e.g., an immunosuppressant) or a radioisotope. A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Suitable therapeutic agents for forming conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Binding agents also can be conjugated to a radioisotope, e.g., iodine-131, yttrium-90 or indium-111, to generate cytotoxic radiopharmaceuticals.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

The term "binding" according to the invention preferably relates to a specific binding.

According to the present invention, an agent such as an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-19}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least 10–6 M, $10^{-5}$ M, $10^{-4}$ M, $10^{-3}$ M, $10^{-2}$ M, or $10^{-1}$ M.

An agent such as an antibody is specific for a predetermined target if it is capable of binding to said predetermined target while it is not capable of binding to other targets, i.e. has no significant affinity for other targets and does not significantly bind to other targets in standard assays. According to the invention, an agent is specific for CLDN18.2 if it is capable of binding to CLDN18.2 but is not (substantially) capable of binding to other targets. Preferably, an agent is specific for CLDN18.2 if the affinity for and the binding to such other targets does not significantly exceed the affinity for or binding to CLDN18.2-unrelated proteins such as bovine serum albumin (BSA), casein, human serum albumin (HSA) or non-claudin transmembrane proteins such as MHC molecules or transferrin receptor or any other specified polypeptide.

Preferably, an agent is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an agent to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an agent to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using surface plasmon resonance analytic (e.g. Biacore), using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

In one embodiment, a binding agent of the invention has the ability of binding to CLDN18.2, i.e. the ability of binding to an epitope present in CLDN18.2, preferably an epitope located within the extracellular domains of CLDN18.2, in particular the first extracellular loop, preferably amino acid positions 29 to 78 of CLDN18.2. In particular embodiments, an agent having the ability of binding to CLDN18.2 binds to an epitope on CLDN18.2 which is not present on CLDN18.1.

An agent having the ability of binding to CLDN18.2 preferably binds to CLDN18.2 but not to CLDN18.1. Preferably, an agent having the ability of binding to CLDN18.2 is specific for CLDN18.2. Preferably, an agent having the ability of binding to CLDN18.2 binds to CLDN18.2 expressed on the cell surface. In particular preferred embodiments, an agent having the ability of binding to CLDN18.2 binds to native epitopes of CLDN18.2 present on the surface of living cells.

In a preferred embodiment, a binding domain for CLDN18.2 or binding agent to CLDN18.2 comprises the following combination of heavy chain variable region (VH) and light chain variable region (VL):

The VH comprises an amino acid sequence represented by SEQ ID NO: 2 or a fragment thereof and the VL comprises an amino acid sequence represented by SEQ ID NO: 3 or a fragment thereof.

In a preferred embodiment, a binding domain for CLDN18.2 or binding agent to CLDN18.2 comprises the following combination of heavy chains and light chains:

The heavy chain comprises an amino acid sequence represented by SEQ ID NO: 12 or a fragment thereof and the light chain comprises an amino acid sequence represented by SEQ ID NO: 13 or a fragment thereof.

In a preferred embodiment, a binding domain for CLDN18.2 or binding agent to CLDN18.2 comprises the following set of complementarity-determining regions CDR1, CDR2 and CDR3: VH: CDR1: positions 45-52 of SEQ ID NO: 12, CDR2: positions 70-77 of SEQ ID NO: 12, CDR3: positions 116-126 of SEQ ID NO: 12, VL: CDR1: positions 47-58 of SEQ ID NO: 13, CDR2: positions 76-78 of SEQ ID NO: 13, CDR3: positions 115-123 of SEQ ID NO: 13.

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment a binding agent comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding agents made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment a binding agent comprising one or more CDRs, a set of CDRs or a combination of sets of CDRs as described herein comprises said CDRs in a human antibody framework.

The CD3 (cluster of differentiation 3) complex denotes an antigen that is expressed on mature human T-cells, thymocytes and a subset of natural killer cells as part of the multimolecular T-cell receptor (TCR) complex. The T-cell co-receptor is a protein complex and is composed of four distinct chains. In mammals, the complex contains a CD3γ chain, a CD3δ chain, and two CD3ε chains. These chains associate with a molecule known as the T-cell receptor (TCR) and the chain to generate an activation signal in T lymphocytes. The TCR, ζ-chain, and CD3 molecules together comprise the TCR complex.

CD3 is responsible for the signal transduction of the TCR. As described by Lin and Weiss, Journal of Cell Science 114, 243-244 (2001), activation of the TCR complex by binding of MHC-presented specific antigen epitopes results in the phosphorylation of immunoreceptor tyrosine-based activation motifs (ITAMs) by Src family kinases, triggering recruitment of further kinases which results in T cell activation including $Ca^{2+}$ release. Clustering of CD3 on T cells, e.g. by immobilized anti-CD3-antibodies, leads to T cell activation similar to the engagement of the T cell receptor, but independent from its clone typical specificity.

As used herein, "CD3" includes human CD3 and denotes an antigen that is expressed on human T cells as part of the multimolecular T cell receptor complex.

With respect to CD3, the binding agent of the invention preferably recognizes the epsilon-chain of CD3, particular, it recognizes an epitope that corresponds to the first 27 N-terminal amino acids of CD3 epsilon or functional fragments of this 27 amino acid stretch.

Anti-CD3 antibodies which are useful for providing binding agents binding to CD3 include but are not limited to UCHT1-HS (humanized mAB), UCHT1-MM (murine mAB), CLB-T3, TR66, 145-2C11.

UCHT1 is a monoclonal IgG1 anti-CD3 monoclonal antibody which detects CD3 in human and primate sample types. CLB-T3 is a mouse monoclonal anti-CD3 antibody which is directed against the CD3 antigen and reacts with 80-90% human peripheral T lymphocytes and medullary thymocytes. TR66 is a mouse IgG1 monoclonal anti-CD3 antibody which recognizes the epsilon-chain of human CD3. 145-2C11 is an armenian hamster monoclonal anti-mouse CD3 antibody.

Preferably, the VH and VL regions of the CD3-binding domain are derived from antibodies/antibody molecules and antibody-like molecules which are capable of specifically recognizing the human CD3 in the context of other TCR subunits as present on activated primary human T cells expressing the TCR in its native configuration. The VH and VL regions derived from an antibody specific for the CD3-epsilon chain are most preferred and said (parental) antibodies should be capable of specifically binding epitopes reflecting the native or near-native structure or a conformational epitope of human CD3 presented in the context of the TCR complex. In a preferred embodiment of the invention, the VH and VL regions of the CD3-binding domain are derived from a CD3 specific antibody selected from the group consisting of UCHT1-HS, UCHT1-MM, CLB-T3 and TR66, preferably TR66.

Antibodies described herein for e.g. providing VL and VH regions can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Nonlabeled murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

It is to be understood that the peptide mimotopes and/or binding agents described herein may be delivered to a patient by administering a nucleic acid such as RNA encoding the peptide mimotope and/or binding agent and/or by administering a host cell comprising a nucleic acid such as RNA encoding the peptide mimotope and/or binding agent. Thus, a nucleic acid encoding a peptide mimotope and/or binding agent when administered to a patient may be present in naked form or in a suitable delivery vehicle such as in the form of liposomes or viral particles, or within a host cell. The nucleic acid provided can produce the peptide mimotope and/or binding agent over extended time periods in a sustained manner. Nucleic acids to be delivered to a patient can be produced by recombinant means. If a nucleic acid is administered to a patient without being present within a host cell, it is preferably taken up by cells of the patient for expression of the peptide mimotope and/or binding agent encoded by the nucleic acid. If a nucleic acid is administered to a patient while being present within a host cell, it is preferably expressed by the host cell within the patient so as to produce the peptide mimotope and/or binding agent encoded by the nucleic acid.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes at least one of said transgenes encoding the peptide mimotope/binding agent described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment the 3'-UTR is derived from the human β-globin gene.

Preferably, RNA if delivered to, i.e. transfected into, a cell, in particular a cell present in vivo, expresses the protein or peptide it encodes.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "RNA encoding" means that RNA, if present in the appropriate environment, preferably within a cell, can be expressed to produce a protein or peptide it encodes.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

According to the invention, a peptide may include natural amino acids and non-natural amino acids. In one embodiment, a peptide merely includes natural amino acids.

According to the invention, the term "non-natural amino acid" refers to an amino acid having a structure different from those of the 20 natural amino acid species. Since non-natural amino acids have structures similar to those of natural amino acids, non-natural amino acids may be classified as derivatives or analogs of given natural amino acids.

According to the invention, the term "cyclic peptide" relates to a peptide or polypeptide chain which forms a ring. A peptide can be cyclized in four different ways: head-to-tail (C-terminus to N-terminus), head-to-side chain, side chain-to-tail or side-chain-to-side-chain. Particularly preferred according to the invention are peptides containing two or more residues containing thiol groups such as cysteines which can form intramolecular disulphide bridges giving cyclic peptides.

According to the invention, a peptide mimotope may be covalently or non-covalently bound to one or more other compounds. Such compounds include peptidic compound such as peptides and proteins as well as non-peptidic compounds such as polyethylene glycol (PEG).

In one embodiment, the peptide mimotopes described herein are PEGylated. PEGylation is the process of covalent attachment of polyethylene glycol (PEG) polymer chains to another molecule, such as a peptide or protein. The covalent attachment of PEG can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding to a target or to sustain effector functions. Preferably, a sequence which is a variant with respect to a specific sequence, when it replaces the specific sequence in an antibody retains binding of said antibody to CLDN18.2 and preferably functions of said antibody as described herein, e.g. CDC mediated lysis or ADCC mediated lysis.

It will be appreciated by those skilled in the art that in particular the sequences of the CDR, hypervariable and variable regions can be modified without losing the ability to bind CLDN18.2. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid can express the nucleic acid.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

The peptide mimotopes described herein may be used in assays for assaying the presence or amount of CLDN18.2 or CLDN18.2 antibodies, in particular the CLDN18.2 antibodies described herein. Such assays may be carried out in a number of ways, including but not limited to immunodetection, and include ELISA, in particular peptide ELISA, competitive binding assays, and the like. In general, in such assays an antibody or antibody fragment is used that specifically binds the target peptide or protein and that is directly or indirectly bound to a label that provides for detection, e.g. indicator enzymes, radiolabels, fluorophores, or paramagnetic particles. The methods of the invention allow quantitative and/or qualitative evaluations, e.g., absolute and/or relative evaluations, of CLDN18.2 or CLDN18.2 antibodies.

The term "enzyme-linked immunosorbent assay or ELISA", as used herein, relates to a method for quantitatively or semi-quantitatively determining protein concentrations from a sample, e.g. blood plasma, serum or cell/tissue extracts, in a multi-well plate format (usually 96-wells per plate). Broadly, proteins in solution are adsorbed to ELISA plates. Antibodies specific for the protein of interest may be used to probe the plate. Background is minimized by optimizing blocking and washing methods (as for IHC), and specificity is ensured via the presence of positive and negative controls. Detection methods are usually colorimetric or chemiluminescence based.

According to the invention, a label may function to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Labels comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

The term "sample", as used herein, includes any biological sample which may be isolated from a patient and used for analysis purposes. Said sample may be a body fluid sample, a tissue sample, or a cell sample. For example, samples encompassed by the present invention are tissue (e.g. section or explant) samples, single cell samples, cell colony samples, cell culture samples, blood (e.g. whole blood or blood fraction such as blood cell fraction, serum or plasma) samples, urine samples, or samples from other peripheral sources. Said samples may be mixed or pooled, e.g. a sample may be a mixture of a blood sample and a urine sample. Said samples may be provided by removing a body fluid, cell(s), cell colonies, an explant, or a section from a patient, but may also be provided by using a previously isolated sample. For example, a tissue sample may be removed from a patient by conventional biopsy techniques or a blood sample may be taken from a patient by conventional blood collection techniques. The sample, e.g. tissue sample or blood sample, may be obtained from a patient prior to initiation of the therapeutic treatment, during the therapeutic treatment, and/or after the therapeutic treatment.

In one embodiment, the sample is a body fluid sample. The term "body fluid sample", as used herein, refers to any liquid sample derived from the body of a patient. Said body fluid sample may be a blood sample, urine sample, sputum sample, breast milk sample, cerebrospinal fluid (CSF) sample, cerumen (earwax) sample, endolymph sample, perilymph sample, gastric juice sample, mucus sample, peritoneal fluid sample, pleural fluid sample, saliva sample, sebum (skin oil) sample, semen sample, sweat sample, tears sample, vaginal secretion sample, or vomit sample including components or fractions thereof. Said body fluid samples may be mixed or pooled. Thus, a body fluid sample may be a mixture of a blood and a urine sample or a mixture of a blood and cerebrospinal fluid sample. Said body fluid sample may be provided by removing a body liquid from a patient, but may also be provided by using previously isolated body fluid sample material.

In one preferred embodiment, the sample is a whole blood sample or a blood fraction sample such as a blood cell fraction, blood serum, or blood plasma sample.

The agents such as peptide mimotopes described herein may be administered in the form of any suitable pharmaceutical composition.

The pharmaceutical compositions of the invention are preferably sterile and contain an effective amount of the agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavouring agents, or colorants.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by an altered expression pattern of CLDN18.2.

For example, in one embodiment, agents described herein can be used to treat a patient with a cancer disease, e.g., a cancer disease such as described herein characterized by the presence of cancer cells expressing CLDN18.2.

The pharmaceutical compositions and methods of treatment described according to the invention may also be used for immunization or vaccination to prevent a disease described herein.

The pharmaceutical composition of the invention may be administered together with supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolongs or enhances or accelerates an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFa, INF-γ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical composition of the present invention.

The pharmaceutical composition can be administered locally or systemically, preferably systemically.

The term "systemic administration" refers to the administration of an agent such that the agent becomes widely distributed in the body of an individual in significant amounts and develops a desired effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of an agent such that the agent does not pass the intestine. The term "parenteral administration" includes intravenous administration, subcutaneous administration, intradermal administration or intraarterial administration but is not limited thereto.

The present invention is further illustrated by the following examples which are not be construed as limiting the scope of the invention.

EXAMPLES

Example 1: Materials and Methods

Phage Display Selection:

IMAB362 binding peptides were identified by phage display technology using a Ph.D.™-C7C phage display peptide library kit (New England Biolabs) with a solution-phase panning protocol. For the panning 50 µl of Protein A Dynabeads (Invitrogen) were washed once with 1 ml of TBST buffer (50 mM Tris-HCl (pH 7.5), 150 mM NaCl+ 0.1% Tween-20) and subsequently blocked with 1 ml blocking buffer (3% BSA in TBS) for 1 h at 4° C. Afterwards, the beads were washed four times with 1 ml TBS-T buffer. A 100-fold representation of the library (1E+11 phages) was incubated with 100 nM of the antibody for 20 min at RT. Antibody-bound phages were captured with blocked Protein A beads by incubation for 15 min at RT with slight shaking. After incubation, beads were washed ten times with TBST to remove unbound phages. Elution was done by subsequent incubation with 50 µl of 100 mM triethylamine (for 6 min) and 50 µl of 100 mM glycine-HCl, pH 2 (for 10 min). Eluates were combined and immediately neutralized with 100 µl 1 M Tris-HCl, pH 7. Amplification of the neutralized phages was done according to manufacturer's instructions by infection of log-phase ER2738 E. coli cells. Amplified phages were purified from E. coli supernatant also as described in the NEB manual by double PEG precipitation. Purified phages were quantified photometrically and used for subsequent panning rounds. Two additional screening rounds were done with decreased antibody concentration (50 nM) and increased washing stringency (washing with 0.5 Tween).

Single Phage Clone Analysis:

After the third screening round, individual phage clones were generated and tested for target binding in a direct phage ELISA. For this purpose, 1E+12 phages were coated to a 96 well Maxisorp™ plate (Thermo Fisher Scientific) in coating buffer (50 mM sodium carbonate, pH 9.4) for 1 h at 37° C. Eight separate wells were coated per clone. The liquid was discarded and wells were blocked overnight at 4° C. with 300 µl blocking buffer (3% BSA in TBS buffer). After washing twice with 300 µl TBS buffer per well, incubation with 500 nM IMAB362 or control targets Rituximab or huIgG-Fc fragment (Merck Millipore; 100 µl per well, diluted with 0.3% BSA in TBS) was done for 90 min at 4° C. Wells were washed three times with TBS-T and twice with TBS. Afterwards bound phages were detected with HRP conjugated goat anti-human IgG antibody (Sigma-Aldrich, 1:5000 diluted with 0.3% BSA in TBS) and TMB substrate. For sequence analysis phage DNA was isolated using the QIAprep Spin M13 kit (Qiagen).

Peptide-Optimization with Peptide Microarrays:

Peptides were synthesized and printed on peptidemicroarray slides essentially as described previously [Funkner, A. et al., J. Mol. Biol. 2013, 425, 1340-1362]. In brief, the peptides were synthesized using SPOT synthesis [Wenschuh, H. et al., Biopolymers 2000, 55, 188-206] cleaved from the solid support and cyclized (50% DMSO, PBS buffer pH 7-8, RT, 16 hours). Subsequently, all peptides were chemoselectively immobilized on functionalized glass slides as described earlier [Funkner, A. et al., J. Mol. Biol. 2013, 425, 1340-1362]. Each peptide was deposited on the microarray in triplicates.

The microarrays were incubated with 1.0 or 0.1 µg/ml IMAB362 in an HS 4800 microarray processing station (Tecan) for two hours at 30° C., followed by incubation with 1.0 µg/ml fluorescently labelled secondary antibody (Alexa647 anti-human Fc antibody; Jackson Immuno Research). Washing steps were performed prior every incubation step with 0.1% Tween-20 in 1×TBS. After the final incubation step the microarrays were washed (0.05% Tween-20 in 0.1×SSC) and dried in a stream of nitrogen. Each microarray was scanned using a GenePix Autoloader 4200AL (Molecular Devices, Pixel size: 10 µm). Signal intensities were evaluated using GenePix Pro 7.0 analysis software (Molecular Devices). For each peptide, the mean of the three triplicates was calculated.

The lower limit of quantification (LLQ) value was defined as LLQ=meanblank+6*SDblank. It was determined by plotting OD (405 nm) values against IMAB362 concentration in the linear range (0-25 ng/ml) and analysis via linear regression.

Further evaluation of results was performed using the statistical computing and graphics software R (Version 2.15.2, www.r-project.org).

Synthesis of Purified Peptides:

The peptides shown in Table 2 were synthesized by standard Fmoc-based solid-phase-synthesis protocols and purified. All target peptides were obtained with a purity of >80%. See supporting information for details.

Binding Analysis Using Biolayer Interferometry:

Binding analysis was performed using streptavidin (SA) sensors on an Octet Red system (FortéBIO). 5 µg/ml of biotinylated peptides were used for loading (200 µl per sensor). To prevent unspecific binding 1× blocking buffer (Sigma-Aldrich) was used in each step after loading. Remained biotin binding sites on coated streptavidin sensors were blocked using 100 µg/ml biocytin (Sigma-Aldrich) for 5 minutes. For binding mode analysis of different peptides 500 nM IMAB362 antibody was used in the association step.

For $K_D$ analysis the antibody was used in a range of 15.625 to 500 nM (15.625, 31.25, 62.5, 125, 250, 500 nM) for each analyzed peptide. The following program was used:
Baseline: 1000 rpm for 180 sec.
Load: 1000 rpm for 900 sec.
Baseline: 1000 rpm for 180 sec.
Blocking: 1000 rpm for 300 sec.
Association: 1000 rpm for 1200 sec.
Dissociation: 1000 rpm for 1200 sec.
Binding analysis using Peptide ELISA:

For the detection of IMAB362, the CLDN18.2 mimicking peptides were immobilized on streptavidin plates (Nunc) in a concentration of 0.75 µg/ml in PBS buffer for 1 hour at 37° C. Subsequently, the plate was washed three times with washing buffer (0.01% Tween-20 in PBS buffer) before it was blocked with 3% BSA in PBS overnight at 4° C. To detect IMAB362, the blocked plate was washed again three times with washing buffer followed by the addition of IMAB362 and incubation for 30 min at 37° C. After another washing step, it was incubated with an alkaline phosphatase conjugated anti-human Fc antibody (Jackson Immuno Research) for additional 30 min at 37° C. Finally, the plate was washed again before being incubated with 1.5 mg/ml of the substrate PNPP (para-nitrophenyl phosphate) in appropriate substrate buffer (1 M Diethanolamine, 0.05 mM MgCl2, 0.01% sodium azide, pH 9.8) for 30 min at RT in the dark. 3 M KOH was used to stop the enzymatic reaction. Absorbance was measured with a microplate reader (Infinite M200, Tecan). For dual wavelength analysis, 405 nm was chosen as measurement wavelength and 492 nm as reference wavelength. Absorbance values were calculated by subtraction of the measured values for the reference wavelength and for the measurement wavelength. Calculation of apparent $K_D$ values was done by fitting the data with Sigma Plot 10 using a two-site saturation binding model.

To analyze the influence of serum, murine serum taken from Balb/cJ mice or human serum type AB (Lonza) was spiked into the ELISA samples and the assay was performed as described above.

In Vivo Pharmakokinetic Analysis:

IMAB362 (1 mg/mouse, approximately 50 mg/kg in PBS buffer), Rituximab (1 mg/mouse, approximately 50 mg/kg in PBS buffer) or only buffer (PBS) was intravenously injected into 11 weeks old female Balb/cJ mice (6 mice per group). After 8, 24, 48, 72, 144, 168 and 192 hrs, blood samples were taken from two mice of each group for serum preparation. The serum samples were to be measured in the linear range of the assay (approximately 0.3-300 ng/ml). Therefore, the serum samples were diluted 1:50000 with PBS buffer containing 0.2% BSA (0.002% final serum content) and analyzed by peptide ELISA as described above using the 2c mimotope peptide for antibody capturing. An IMAB362 standard row in presence of murine Balb/cJ control serum was assayed in parallel (0-25 ng/ml). The standard raw data were fitted by linear regression to calculate the antibody concentration from the mouse samples at the respective timepoint. Before the pharmakokinetic analysis, a permission for the animal experiment was obtained from the relevant local authority.

Peptide Synthesis
Materials:

All solvents were used without further purification. Water was demineralized with a demineralization system (Milli-Q Plus, Millipore). The reagents were purchased from Advanced ChemTech (Louisville, Ky., USA), Sigma-Aldrich (Deisenhofen, Germany), Bachem (Basel, Schweiz), J.T. Baker (Phillipsburg, USA), NeoMPS (Strassburg, Frankreich), GL Biochem (Shanghai, China) or Merck Chemicals (Nottingham, UK) and used without further purification.

Equipment:

RP-HPLC-MS-analysis was done with an Agilent Series 1200 System (2×1200 Series binary pump SL G1312B, 1200 thermostatted column compartment SL G1316B, 1200 series high perf. autosampler SL G1367C, 1200 series micro-vacuum degasser G1379B, 1100/1200 automation interface G2254A, 1100/1200 wellplate handler G2255A, VWD-UV detector G1314B, valve G1158A,) and coupled ESI-MS (Agilent LC/MSD Quad SL system G1956B) on a Phenomenex Gemini-NX-3u column at 30° C. and a flow of 1.0 ml/min with a linear gradient (5 95% B in 6 min, with A: 0.05% TFA in water and B: 0.05% TFA in MeCN) and UV detection at a wavelength of 220 nm. Preparative separations were done on a Dionex UltiMate 3000 HPLC system with suitable gradients (solvent A: 0.05% TFA in water, solvent B: 0.05% TFA in MeCN) and UV detection at 220 nm.

General Method for Peptide Synthesis:

The C-terminal amino acid (Fmoc-Gly-OH) was coupled to chlorotrityl polystyrene resin (100-400 mg) to yield a loading of approx. 0.3 mmol/g. Following Fmoc deprotection with a solution of piperidine in DMF (15:85, 2×10 min), repeating cycles of coupling of amino acids and Fmoc cleavage were performed until the linear target peptides were assembled. For the coupling of the amino acids the following reagents were employed: Fmoc-AA-OH (3.5 eq.), HOBt (1.0 eq.), DIC (3.5 eq.) in DMF for 75 min. For all amino acids double couplings were performed. Biotin was coupled with the following protocol: Biotin (5.0 eq.), HBTU (5.0 eq.), DIPEA (10.0 eq.) in NMP for 16 hours. The peptides were cleaved off the solid support with TFA/H2O/TIPS/EDT (90:3:4:3, RT, 3 hours) and treated with MTBE at 0° C. The suspension was centrifuged and the supernatant removed to furnish the crude peptides. For cyclization the peptides were dissolved in H2O/MeCN at a concentration of 1 mg/mL. The solutions were brought to pH 7-7.5 by addition of 2 M ammonia in H2O. After addition of DMSO (2%) the solutions were stirred under an air atmosphere for 16-72 hours. Upon completion of the cyclization, which was monitored by LC-MS, the crude reaction mixture was acidified with TFA and lyophilized. Purification was done by dissolution in MeCN/H2O and fractionation by HPLC.

Example 2

Selection of IMAB362-Specific Peptides by Phage Display

Figure 1A:
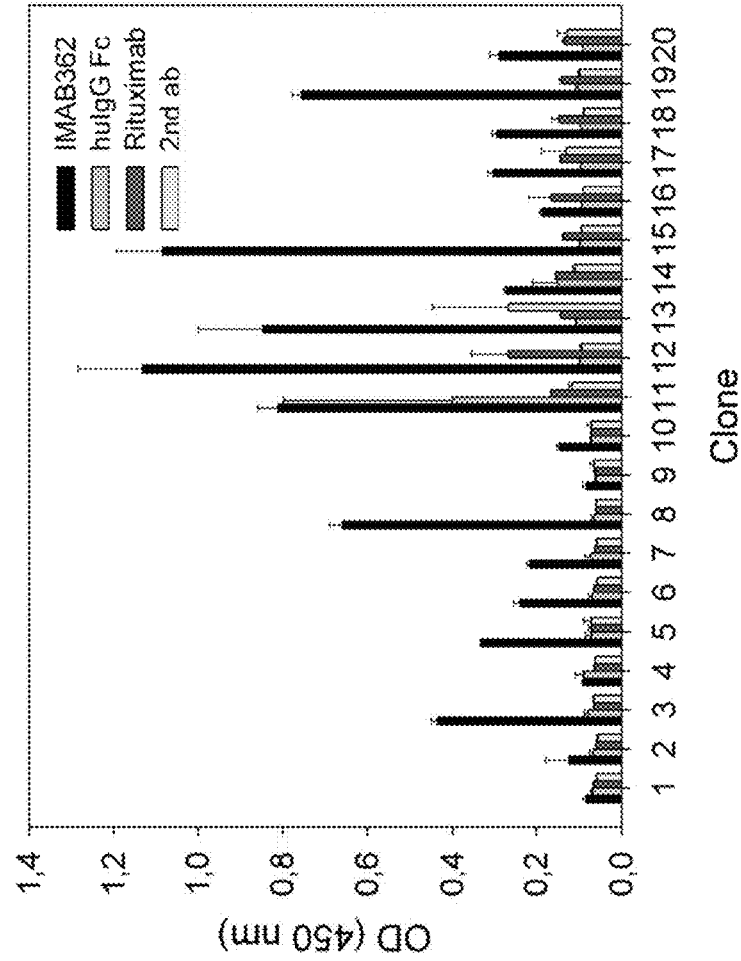
Figure 2:
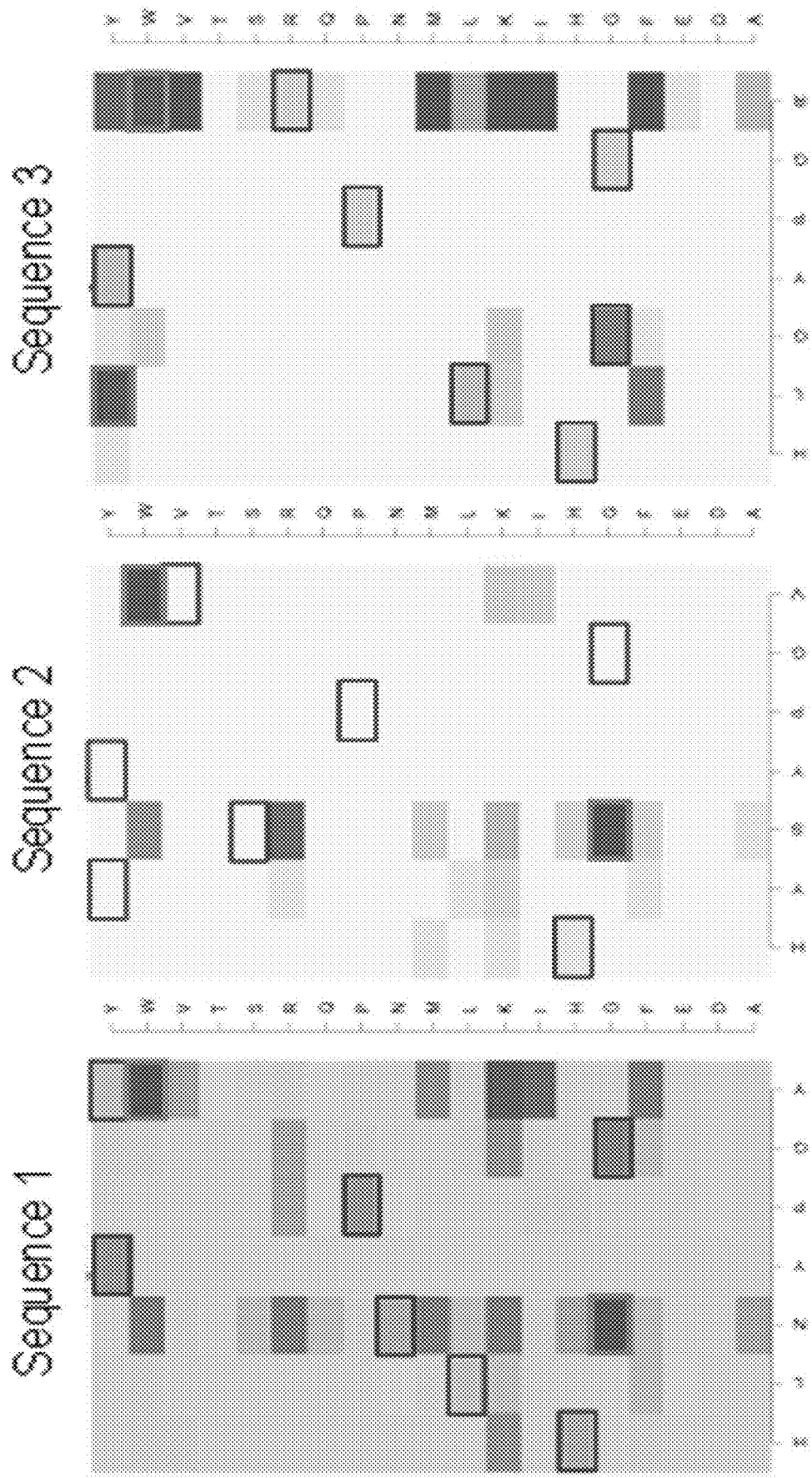
FIG. 2. SAR analysis of IMAB362 binding peptides using peptide microarrays. Shown are the results for substitutional analyses of sequences number 1, 2 and 3. Each amino acid of the starting sequence (shown at the bottom) is substituted by each of the other natural amino acids except Cys, resulting in an overall number of 7×19×3=399 different peptides. Dark colour represents strong signals, shades show weaker signals. The blue boxes indicate the amino acids of the original peptides. The peptides highlighted with green boxes were selected for re-synthesis, purification and detailed binding analysis.

For the identification of IMAB362-binding peptides phage display was performed using a disulfide-constrained random 7mer M13 phage library (New England Biolabs). To ensure good accessibility of the antibody a selection in solution protocol with protein-A bead capture of binding phages was carried out. After three consecutive screening rounds with increased stringency an enrichment of target-specific phages could be observed, measured by dilution plating of input and output phages and phage ELISA (data not shown). Analysis of single clones randomly picked after the 3rd screening round yielded several IMAB362 binders (FIG. 1A). The phage ELISA suggests that the isolated peptides are specific for the variable part of IMAB362, because a control antibody with similar chimeric backbone (Rituximab) and a human IgG Fc fragment were not recognized. DNA sequence analysis of selected clones revealed a common YPG motif (FIG. 1B) in the middle of the sequences. Three of the peptide sequences (sequence 1, 2, and 3; FIG. 1B and Table 1) were selected for further binding and SAR analysis and optimization via peptide microarrays.

promising peptides were performed (peptides 1a, 2a and 3a, Table 1). In total 399 peptides were synthesized, handled, cyclized and immobilized to microarrays as described above. The results after incubation of the peptide microarrays with IMAB362 are shown in FIG. 2. It became apparent that substitution of several amino acids of the starting sequences (sequences number 1, 2 and 3) by alternative amino acids resulted in increased signal intensities. Several

TABLE 1

Peptide microarray incubation: results for assay setup.

| | | % Affinity compared to hit peptide | | |
|---|---|---|---|---|
| Peptide Structure[a] | Concentration[b] | ACHLNYPGYCG (Seq. 1) | ACHYSYPGVCG (Seq. 2) | ACHLGYPGRCG (Seq. 3) |
| Cyclopeptide-GGS-K(X) | 1 | 100 | 100 | 100 |
| X-Ttds-Cyclopeptide | 1 | 95.9 (Peptide 1a) | 98.3 (Peptide 2a) | 107.8 (Peptide 3a) |
| X-Ttds-Cyclopeptide | 0.1 | 2.6 | 22.9 | 11.6 |
| X-Ttds-Linearpeptide | 1 | 0 | 0 | 0.1 |

Shown are the results for nine different peptides (sequences and structures indicated in table).
Affinities were calculated from fluorescence units as percentage of the fluorescence assay signal of the hit peptides identified by phage display.
[a]X is the functional group being used for covalent attachment of the peptides to the microarray.
[b]Concentration of IMAB362 (in µg/ml).

SAR Analysis and Optimization of IMAB362-Specific Peptides by Peptide Microarrays Peptide microarrays were used for structure-activity-relationship (SAR) analysis and optimization of peptide binding affinity to IMAB362. For assay setup three variants of each cyclic hit peptide (sequences 1, 2 and 3, Table 1) were prepared differing in a) the immobilization site, b) the linker nature and c) the degree of conformational restriction (cyclic vs. linear). All peptides were chemically synthesized in a stepwise fashion from the C- to the N-terminus by the high-throughput SPOT synthesis approach [Wenschuh, H. et al., Biopolymers 2000, 55, 188-206] applying a cellulose membrane as solid support. After cleavage and isolation, the peptides were cyclised through disulfide formation between two internal Cys residues and immobilized to the microarray. Covalent attachment to the microarray was performed through a reactive moiety on either the N- or C-terminus of the peptides allowing chemoselective and directed immobilization through both ends of the peptides. Subsequently, peptide loaded microarrays were incubated with 1.0 or 0.1 µg/ml IMAB362 followed by incubation with 1 µg/ml fluorescently labelled secondary antibody, scanning and data evaluation.

The results of the measurements for assay setup on the peptide microarrays are shown in Table 1. The IMAB362 antibody exhibits comparably strong binding to all parental (cyclic, immobilized through C-terminus) peptides examined (Table 1, row 1). The binding was independent from the immobilization site (C- vs. N-terminal immobilization) (Table 1, row 2). As expected, reduction of the IMAB concentration to 0.1 µg/ml (Table 1, row 3) reduced the assay signal. The final experiment (Table 1, row 4) showed that cyclization is essential for binding as none of the linear peptides furnished any signal in the microarray assay.

For peptide optimization substitutional analyses (exchange of parental amino acids at each position by all proteinogenic amino acids except Cys) of the three most promising peptides were performed (peptides 1a, 2a and 3a, Table 1). In total 399 peptides were synthesized, handled, cyclized and immobilized to microarrays as described above. The results after incubation of the peptide microarrays with IMAB362 are shown in FIG. 2. It became apparent that substitution of several amino acids of the starting sequences (sequences number 1, 2 and 3) by alternative amino acids resulted in increased signal intensities. Several sequences showing highest signal intensities were selected for re-synthesis, purification and detailed binding analysis (FIG. 2, green boxes).

Detailed Binding Analysis of Optimized IMAB362-Specific Peptides

Figure 5:
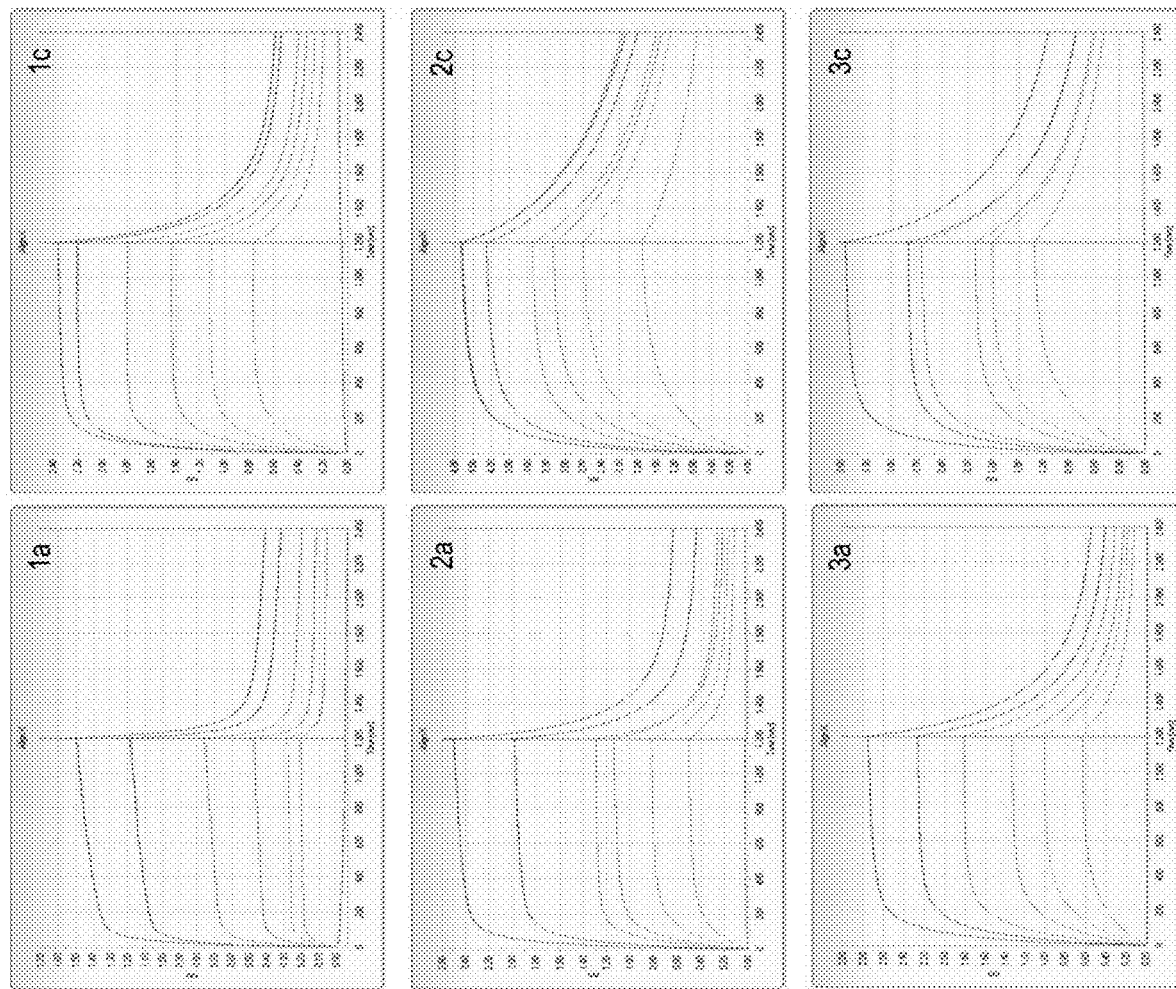
FIG. 5. Biolayer interferometry of IMAB362 antibody interaction with the mimotope peptides (1a, 1c, 2a, 2c, 3a, 3c). Streptavidin biosensors were loaded with 5 µg/ml of the respective biotinylated peptide followed by incubation with different IMAB362 concentrations (15.625, 31.25, 62.5, 125, 250, 500 nM). Shown are association and dissociation curves after initial processing (subtraction of reference, Aligned to baseline).

The peptides displaying the highest binding affinities from the peptide microarray experiments were synthesized by standard Fmoc-based solid-phase-synthesis protocols and purified (HPLC purity: >80%). The binding characteristics of each peptide were determined. ELISA was used for assessment of the thermodynamic behaviour, while biolayer interferometry (BLI) was applied to the strongest binders for kinetic analysis (see also FIG. 5).

The results of the measurements shown in Table 2 indicate that the affinity of each of the three parental peptides (peptides 1a, 2a and 3a) could be significantly improved. Correspondingly, BLI data show the following improvements of affinity: peptide 1a (810 nM) to peptide 1c (108 nM), peptide 2a (100 nM) to peptide 2c (52 nM) and peptide 3a (320 nM) to peptide 3c (92 nM). In the ELISA assay considerably improved IC50 values were measured: peptide 1a (5.80 nM) to peptide 1c (0.26 nM), peptide 2a (4.44 nM) to peptide 2c (0.15 nM) and peptide 3a (1.61 nM) to peptide 3c (0.13 nM).

TABLE 2

Binding characteristics of parental and maturated peptides

| Peptide | Sequence[a] | Apparent $K_D$, ELISA[b] [nM] | Apparent $K_D$, BLI[c] [nM] |
|---|---|---|---|
| 1a | Biotin-Ttds-ACHLNYPGYCG-OH | 5.80 | 810 |
| 1b | Biotin-Ttds-ACHLNYPGWCG-OH | 0.28 | n.d. |
| 1c | Biotin-Ttds-ACHLGYPGYCG-OH | 0.26 | 108 |
| 2a | Biotin-Ttds-ACHYSYPGVCG-OH | 4.44 | 100 |
| 2b | Biotin-Ttds-ACHYSYPGWCG-OH | 2.12 | n.d. |

TABLE 2-continued

Binding characteristics of parental and maturated peptides

| Peptide | Sequence[a] | Apparent $K_D$, ELISA[b] [nM] | Apparent $K_D$, BLI[c] [nM] |
|---|---|---|---|
| 2c | Biotin-Ttds-ACHYGYPGVCG-OH | 0.15 | 52 |
| 3a | Biotin-Ttds-ACHLGYPGRCG-OH | 1.61 | 320 |
| 3b | Biotin-Ttds-ACHYGYPGRCG-OH | 0.57 | n.d. |
| 3c | Biotin-Ttds-ACHLGYPGWCG-OH | 0.13 | 92 |

Shown are the apparent binding constants for the parental and maturated IMAB362 binding peptides.
[a]All peptides were cyclized by Cys-Cys-disulfide bond formation. Ttds is a linker with the following structure: 1,13-diamino-4,7,10-trioxatridecan-succinamic acid. Amino acids that were exchanged compared to the original sequence are underlined.
[b]Shown values are the mean of at least two individual measurements.
[c]Measurement of at least six different concentrations of IMAB362 over a time period of each 1200 sec. for association and dissociation. n.d. = not determined.

Figure 3A:
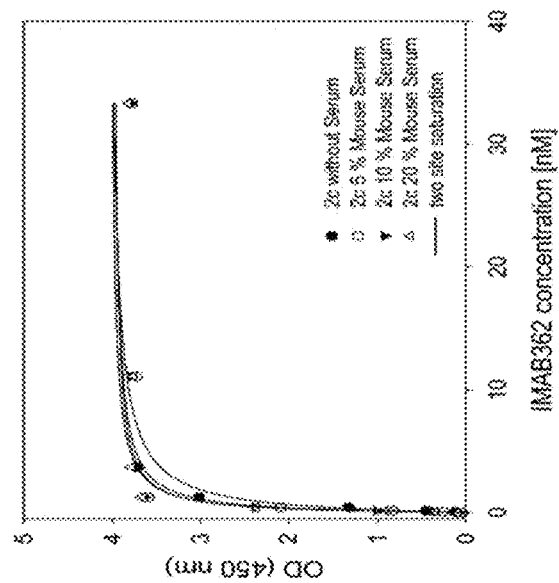
FIGS. 3A, 3B, and 3C. Peptide ELISA with and without serum incubation.
Figure 3B:
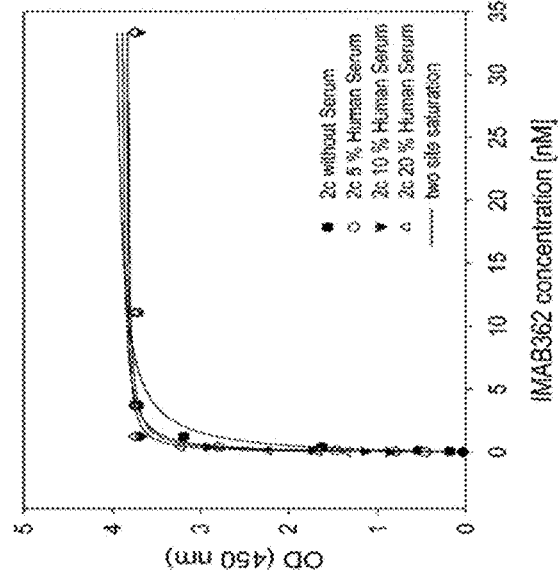
Figure 3C:
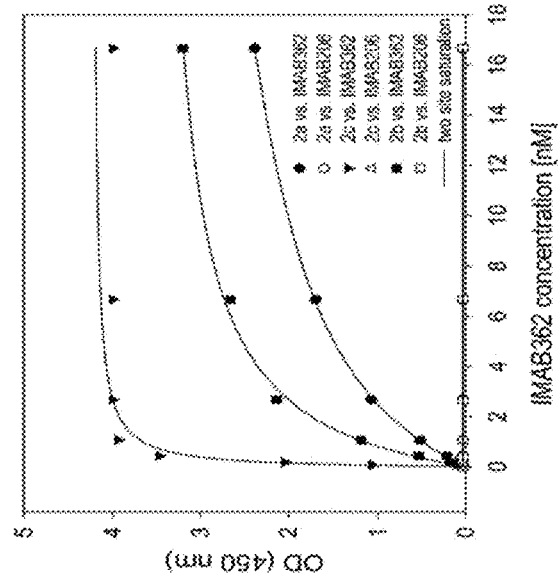

For the development of an optimal detection system for IMAB362 in biological samples the peptide 2 group (peptides 2a, 2b and 2c, Table 2) was chosen for detailed peptide ELISA analysis, because peptide 2c is the most affine variant when considering BLI and ELISA data. For this purpose, the peptides were immobilized on streptavidin coated 96-well plates and binding of IMAB362 and a similar control antibody were measured by ELISA. FIG. 3A shows the binding curves of the three peptides by comparison. To simulate the situations of a pharmakokinetic study the most affine peptide 2c was also analyzed in the presence of up to 20% human or mouse serum (FIGS. 3B and 3C). It became evident that binding of IMAB362 to peptide 2c is almost not affected by mouse serum components. The binding curves looked similar when the antibody was diluted with human serum although the background signal was slightly increased especially at high serum concentrations.

Figure 4:
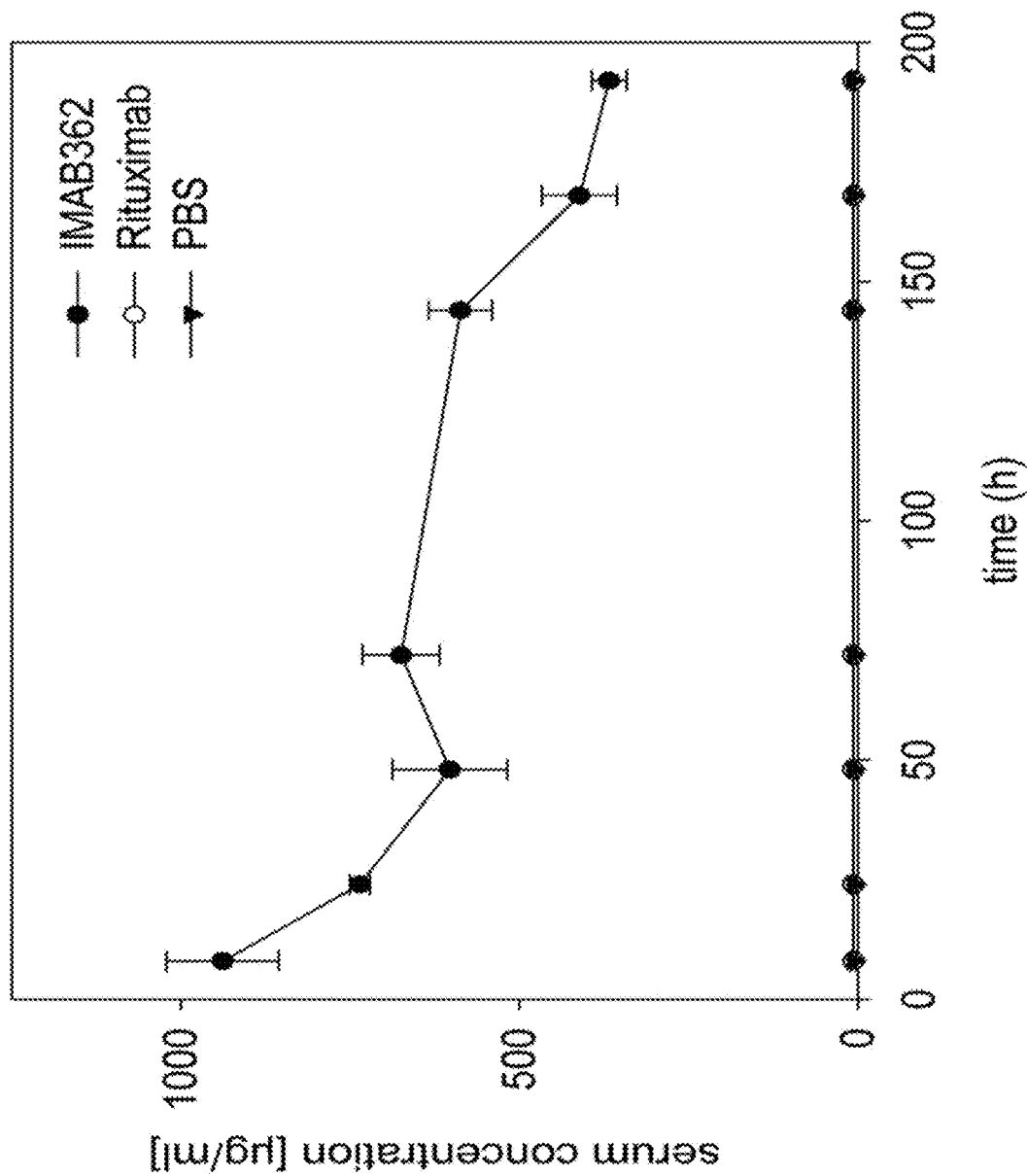
FIG. 4. Pharmacokinetic analysis of IMAB362 using the established peptide ELISA assay. IMAB362, Rituximab or PBS buffer only were intravenously injected into Balb/-cJ mice. Blood samples were taken over a period of 8 consecutive days and analyzed via peptide ELISA with the 2c mimotope peptide for antibody capturing. Median values of two mice per timepoint for each group are shown and SD is presented as error bars for each timepoint.

Use of IMAB362-Specific Peptides for the Detection of IMAB362 in Serum Samples from a Pharmacokinetic Study To prove the applicability of the developed assay a pharmacokinetic study was carried out. For this purpose, IMAB362 (approximately 50 mg/kg in PBS buffer), Rituximab (approximately 50 mg/kg in PBS buffer) or PBS buffer only were injected into Balb-cJ mice. Blood samples were taken after different time points (8, 24, 48, 72, 144 and 192 hrs) and subsequently analyzed by peptide ELISA using the 2c mimotope peptide for capturing of the antibody. FIG. 4 shows a decrease of the IMAB362 concentration in mice over time starting from approximately 800 µg/ml after 8 hours to approximately 350 µg/ml at the end of the study. All control samples from the Rituximab and the PBS mice groups were negative, which illustrates the high specificity of the developed assay.

Example 3: Influence of CLDN18.2 Mimotope on BiMAB Binding to NugC4 TargEt Cells and NugC4 Target Cell Lysis Cell Culture The human gastric cancer cell line NugC4 was derived from the Japanese Collection of Research Bioresources and has been stably transduced with the human CLDN18.2 gene in addition to a stable transfection with the firefly luciferase gene. The cells were cultivated in RPMI complete medium containing 10% FBS at 37° C. in a 7.5% CO2 humidified incubator.

Preparation of Primary Human T-Cells

Human T-cells were freshly isolated from human blood from healthy donors according to standard procedures (Current Protocols in Immunology, 2012): briefly, blood was diluted with DPBS, layered on Ficoll-Paque Plus (GE Healthcare Life Sciences) and centrifuged. Peripheral blood mononuclear cells (PBMC) were collected from the interphase, washed with cold DPBS supplemented with 2 mM EDTA and counted. Human T-cells were subsequently separated by magnetic-activated cell separation (MACS) from PBMCs by Pan T-Cell Isolation Kit II (Miltenyi Biotec) according to the manufacturer's guidelines.

Cytotoxicity Assay

To determine BiMAB-mediated lysis of CLDN18.2-expressing NugC4 target cells by primary human T-cells, a luminescence-based cytotoxicity assay was performed. Human T-cells were prepared as described above. NugC4 cells stably expressing the luciferase gene were used as target cells. 1×104 target cells were seeded per well into white flat bottom 96-well plates. Human T cells were added in an E:T ratio of 5:1. RPMI complete medium+10% FBS was used to adjust the final volume to 100 µl. Test samples and control samples were plated at least in triplicates.

Cell culture microplates were incubated for 24 h at 37° C., 5% CO2. Afterwards, 50 µl of a aqueous solution containing 1 mg/ml luciferin (BD Monolight, BD Biosciences) and 50 mM HEPES were added per well and plates subsequently incubated for 30 min in the dark at 37° C. Luminescence arising from oxidation of luciferin by luciferase expressing viable cells was measured in a microplate-reader (Infinite M200, Tecan). Percentage of specific target cell lysis was calculated by the following formula: % specific lysis=[1−(luminescencetest sample−Lmax)/(Lmin−Lmax)]×100, whereas "L" indicates lysis. Lmin refers to the minimum lysis in the absence of bi-scFv and Lmax to the maximum lysis (equal to spontaneous luminescence counts) in the absence of bi-scFv achieved by addition of Triton X-100 (2% final concentration).

Cell Binding Assay

To assess the cancer target cell binding of a bispecific single chain antibody specific for CLDN18.2 on cancer target cells, 2×105 NugC4 cells were incubated 30 min with 100, 1000 or 10000 ng/ml BiMAB in a final volume of 100 µl at 4° C. Afterwards, cells were washed with 2 ml DPBS followed by staining with 3.3 µg/ml of an anti-His antibody (Dianova) for additional 30 min at 4° C. before. Subsequently, cells were washed again with 2 ml DPBS and stained with an allophycocyanin-conjugated anti-mouse antibody (BD Biosciences) for 10 minutes at 4° C. Finally, cells were washed twice with 2 ml DPBS before the mean fluorescence intensity was measured at FACS canto II (Becton Dickinson).

Figure 6A:
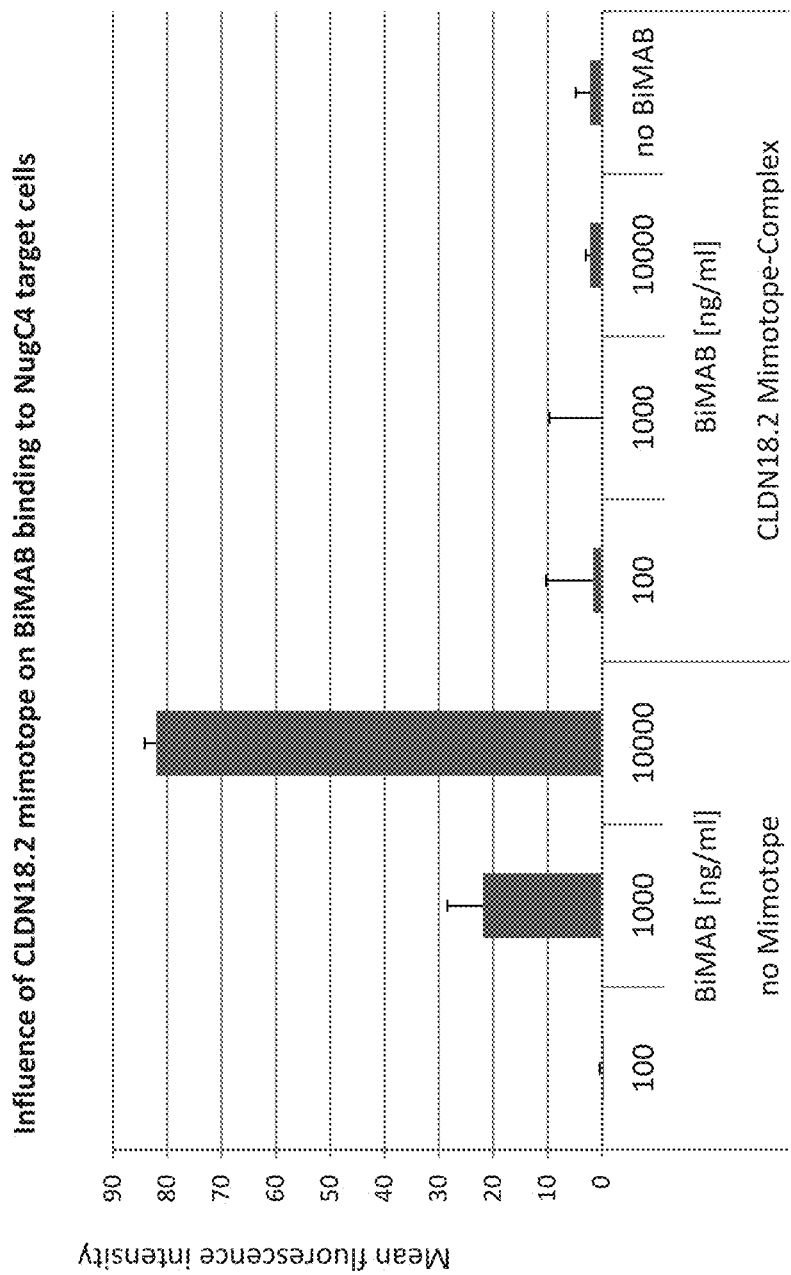
FIG. 6A and FIG. 6B. Effect of mimotopes on BiMAB-mediated effects.
Figure 6B:
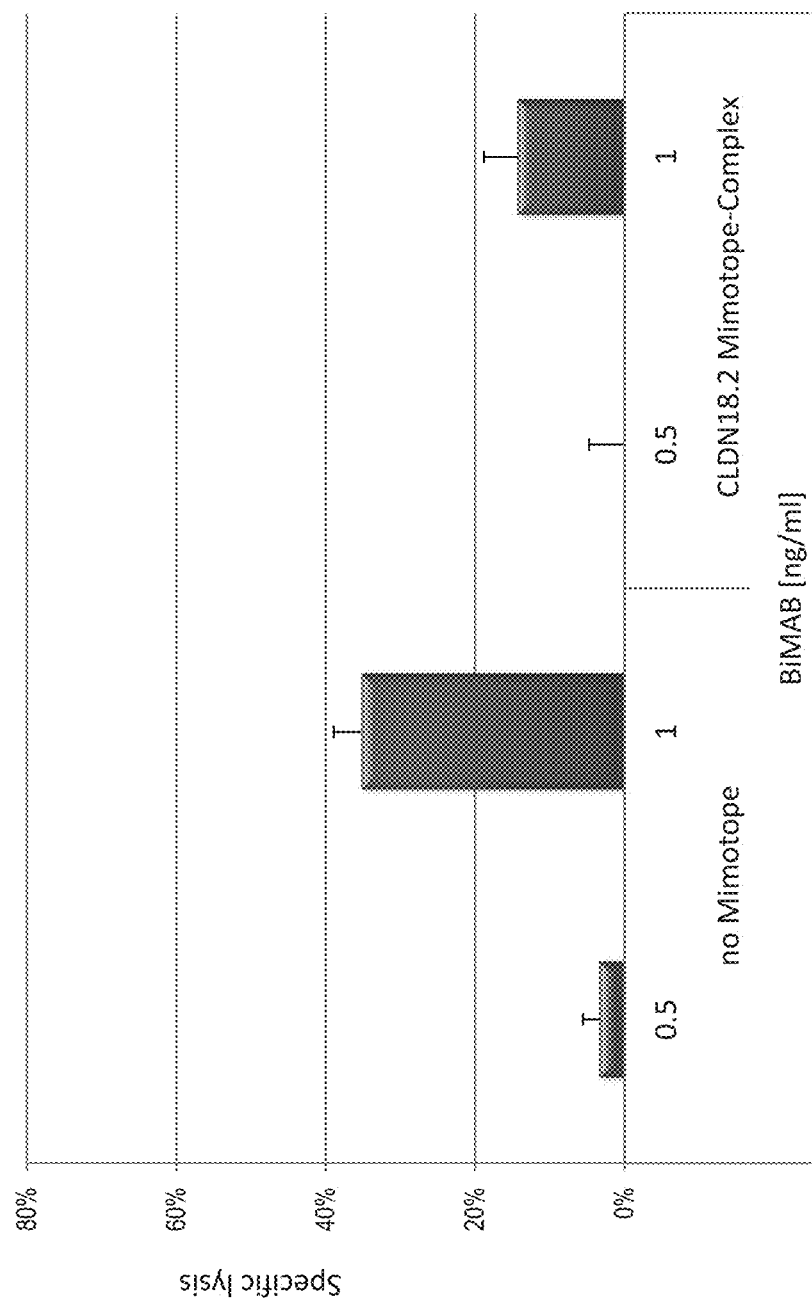

FIG. 6 shows the influence of CLDN18.2 mimotope on BiMAB binding to NugC4 target cells and NugC4 target cell lysis.

The invention claimed is:

1. A peptide mimotope of claudin 18.2 (CLDN18.2) comprising the amino acid sequence Cys Xaa1 Xaa2 Xaa3 Tyr Pro Gly Xaa4 Cys    (SEQ ID NO: 19), wherein
Xaa1 is an amino acid selected from the group consisting of Lys, Met, His, and Tyr,
Xaa2 is an amino acid selected from the group consisting of Leu, Lys, Tyr, Arg, and Phe,
Xaa3 is an amino acid selected from the group consisting of Gly, Asn, Arg, Ser, Trp, and Lys, and
Xaa4 is an amino acid selected from the group consisting of Trp, Tyr, Glu, Arg, Val, Lys, Ile, Met, and Phe,
wherein the thiol group of said cysteine residues form an intramolecular disulfide bridge.

2. The peptide mimotope of claim 1, which comprises the amino acid sequence selected from the group consisting of:

Cys His Leu Gly Tyr Pro Gly Arg Cys    (SEQ ID NO: 37),

Cys His Tyr Gly Tyr Pro Gly Arg Cys    (SEQ ID NO: 38),

Cys His Leu Gly Tyr Pro Gly Trp Cys    (SEQ ID NO: 39),

Cys His Tyr Ser Tyr Pro Gly Val Cys    (SEQ ID NO: 40),

Cys His Tyr Gly Tyr Pro Gly Val Cys    (SEQ ID NO: 41),

| | |
|---|---|
| Cys His Tyr Ser Tyr Pro Gly Trp Cys | (SEQ ID NO: 42), |
| Cys His Leu Arg Tyr Pro Gly Glu Cys | (SEQ ID NO: 43), |
| Cys His Tyr Arg Tyr Pro Gly Glu Cys | (SEQ ID NO: 44), |
| Cys His Leu Asn Tyr Pro Gly Tyr Cys | (SEQ ID NO: 45), |
| Cys His Leu Gly Tyr Pro Gly Tyr Cys | (SEQ ID NO: 46), |
| Cys His Leu Asn Tyr Pro Gly Trp Cys | (SEQ ID NO: 47), |
| Cys Tyr Lys Gly Tyr Pro Gly Tyr Cys | (SEQ ID NO: 48), and |
| Cys His Tyr Gly Tyr Pro Gly Trp Cys | (SEQ ID NO: 49). |

3. The peptide mimotope of claim 1, wherein:
Xaa1 is an amino acid selected from the group consisting of His and Tyr;
Xaa2 is an amino acid selected from the group consisting of Leu, Lys, Tyr, and Phe;
Xaa3 is an amino acid selected from the group consisting of Gly, Asn, Arg, Ser, Trp, and Lys; and
Xaa4 is an amino acid selected from the group consisting of Trp, Tyr, Glu, Arg, Val, Lys, Ile, Met, and Phe.

4. The peptide mimotope of claim 1, wherein:
Xaa1 is an amino acid selected from the group consisting of His and Tyr;
Xaa2 is an amino acid selected from the group consisting of Leu, Lys, and Tyr;
Xaa3 is an amino acid selected from the group consisting of Gly, Asn, Arg, and Ser; and
Xaa4 is an amino acid selected from the group consisting of Trp, Tyr, Glu, Arg, and Val.

5. The peptide mimotope of claim 1, wherein:
Xaa1 is His;
Xaa2 is Tyr;
Xaa3 is Gly; and
Xaa4 is Val.

6. The peptide mimotope of claim 1, wherein the peptide mimotope is characterized as a competitor of CLDN18.2 for binding to a CLDN18.2 binding domain.

7. The peptide mimotope of claim 1, wherein the peptide mimotope is part of a fusion polypeptide.

8. The peptide mimotope of claim 1, wherein the peptide mimotope is conjugated to at least one fusion partner.

9. The peptide mimotope of claim 8, wherein the fusion partner comprises a heterologous amino acid sequence.

10. The peptide mimotope of claim 8, wherein the fusion partner comprises a reporter for an immunological assay or a label.

11. A recombinant nucleic acid which encodes a peptide mimotope of claim 1.

12. A host cell comprising the recombinant nucleic acid of claim 11.

13. A peptide mimotope of claim 18.2 (CLDN18.2) comprising the amino acid sequence

| | |
|---|---|
| Ala Cys Xaa1 Xaa2 Xaa3 Tyr Pro Gly Xaa4 Cys Gly | (SEQ ID NO: 21), | wherein
Xaa1 is an amino acid selected from the group consisting of Lys, Met, His, and Tyr;
Xaa2 is an amino acid selected from the group consisting of Leu, Lys, Tyr, Arg, and Phe;
Xaa3 is an amino acid selected from the group consisting of Gly, Asn, Arg, Ser, Trp, and Lys; and
Xaa4 is an amino acid selected from the group consisting of Trp, Tyr, Glu, Arg, Val, Lys, Ile, Met, and Phe,
wherein the thiol group of said cysteine residues form an intramolecular disulfide bridge.

14. The peptide mimotope of claim 13, wherein:
Xaa1 is an amino acid selected from the group consisting of His and Tyr;
Xaa2 is an amino acid selected from the group consisting of Leu, Lys, and Tyr;
Xaa3 is an amino acid selected from the group consisting of Gly, Asn, Arg, and Ser; and
Xaa4 is an amino acid selected from the group consisting of Trp, Tyr, Glu, Arg, and Val.

15. The peptide mimotope of claim 13, which comprises the amino acid sequence selected from the group consisting of:

| | |
|---|---|
| Ala Cys His Leu Gly Tyr Pro Gly Arg Cys Gly | (SEQ ID NO: 51), |
| Ala Cys His Tyr Gly Tyr Pro Gly Arg Cys Gly | (SEQ ID NO: 52), |
| Ala Cys His Leu Gly Tyr Pro Gly Trp Cys Gly | (SEQ ID NO: 53), |
| Ala Cys His Tyr Ser Tyr Pro Gly Val Cys Gly | (SEQ ID NO: 54), |
| Ala Cys His Tyr Gly Tyr Pro Gly Val Cys Gly | (SEQ ID NO: 55), |
| Ala Cys His Tyr Ser Tyr Pro Gly Trp Cys Gly | (SEQ ID NO: 56), |
| Ala Cys His Leu Arg Tyr Pro Gly Glu Cys Gly | (SEQ ID NO: 57), |
| Ala Cys His Tyr Arg Tyr Pro Gly Glu Cys Gly | (SEQ ID NO: 58), |
| Ala Cys His Leu Asn Tyr Pro Gly Tyr Cys Gly | (SEQ ID NO: 59), |
| Ala Cys His Leu Gly Tyr Pro Gly Tyr Cys Gly | (SEQ ID NO: 60), |
| Ala Cys His Leu Asn Tyr Pro Gly Trp Cys Gly | (SEQ ID NO: 61), |
| Ala Cys Tyr Lys Gly Tyr Pro Gly Tyr Cys Gly | (SEQ ID NO: 62), and |
| Ala Cys His Tyr Gly Tyr Pro Gly Trp Cys Gly | (SEQ ID NO: 63). |

* * * * *